US008969014B2

(12) United States Patent
Nordlund

(10) Patent No.: US 8,969,014 B2
(45) Date of Patent: Mar. 3, 2015

(54) METHODS FOR DETERMINING LIGAND BINDING TO A TARGET PROTEIN USING A THERMAL SHIFT ASSAY

(71) Applicant: Evitraproteoma AB, Stockholm (SE)

(72) Inventor: Pár Nordlund, Stockholm (SE)

(73) Assignee: Evitraproteoma AB, Stockholm (SE)

( * ) Notice: Subject to any disclaimer, the term of this patent is extended or adjusted under 35 U.S.C. 154(b) by 0 days.

(21) Appl. No.: 14/057,920

(22) Filed: Oct. 18, 2013

(65) Prior Publication Data

US 2014/0057368 A1    Feb. 27, 2014

Related U.S. Application Data

(63) Continuation of application No. PCT/GB2012/050853, filed on Apr. 18, 2012.

(30) Foreign Application Priority Data

Apr. 18, 2011    (GB) .................................. 1106548.9

(51) Int. Cl.
| | |
|---|---|
| *G01N 33/53* | (2006.01) |
| *G01N 33/68* | (2006.01) |
| *G01N 33/94* | (2006.01) |

(52) U.S. Cl.
CPC ............ *G01N 33/68* (2013.01); *G01N 33/6845* (2013.01); *G01N 33/9446* (2013.01); *G01N 33/9453* (2013.01); *G01N 33/946* (2013.01); *G01N 33/9466* (2013.01); *G01N 33/9473* (2013.01); *G01N 33/948* (2013.01); *G01N 33/9486* (2013.01); *G01N 33/9493* (2013.01)
USPC ............................................ 435/7.1; 435/7.2

(58) Field of Classification Search
None
See application file for complete search history.

(56) References Cited

U.S. PATENT DOCUMENTS

| | | | |
|---|---|---|---|
| 6,036,920 | A | 3/2000 | Pantoliano et al. |
| 6,171,850 | B1 | 1/2001 | Nagle et al. |
| 2002/0114734 | A1 | 8/2002 | Pantoliano et al. |
| 2005/0006372 | A1 | 1/2005 | Murakami et al. |
| 2010/0256342 | A1* | 10/2010 | Salemme et al. .......... 530/391.1 |
| 2011/0124120 | A1 | 5/2011 | Kranz et al. |

FOREIGN PATENT DOCUMENTS

| | | |
|---|---|---|
| EP | 1639373 B1 | 3/2006 |
| WO | 86/06492 A1 | 11/1986 |
| WO | 97/42500 A1 | 11/1997 |
| WO | 99/24050 A1 | 5/1999 |
| WO | 01/46693 A2 | 6/2001 |
| WO | 02/103321 A2 | 12/2002 |
| WO | 2004/101790 A1 | 11/2004 |
| WO | 2005/107938 A2 | 11/2005 |
| WO | 2006/110292 A2 | 10/2006 |
| WO | 2010/151180 A1 | 12/2010 |

OTHER PUBLICATIONS

Cimmperman, Piotras et al., "A Quantitative Model of Thermal Stabilization and Destabilization of Proteins by Ligands," Biophysical Journal, vol. 95:3222-3231 (2008).
Ericsson, U.B. et al., "Thermofluor-based high-throughput stability optimization of proteins for structural studies," Analytical Biochemistry, vol. 357(2):289-298 (2006).
Kim, Jae-Young et al., "Temperature-Triggered Purification of Antibodies," Biotechnology and Bioengineering, vol. 90 (3):373-379 (2005).
Knaust, R.K. et al., "Screening for soluble expression of recombinant proteins in a 96-well format," Analytical Biochemistry, vol. 297(1):79-85 (2001).
Lomenick, Brett et al., "Target identification using drug affinity responsive target stability (DARTS)," PNAS, vol. 106 (51):21984-21989 (2009).
Minagawa, H. et al., "Improving the thermal stability of lactate oxidase by directed evolution," Cell. Mol. Life Sci., vol. 64:77-81 (2007).
Moreau, Morgane J.J. et al., "Quantitative determination of protein stability and ligand binding using a green fluorescent protein reporter system," Molecular Biosystems, vol. 6(7):1285-1292 (2010).
Pantoliano, Michael W. et al., "High-Density Miniaturized Thermal Shift Assays as a General Strategy for Drug Discovery," Journal of Biomolecular Screening, vol. 6(6):429-440 (2001).
Pohn, Brigitte et al., "Micro-colony array based high throughput platform for enzyme library screening," Journal of Biotechnology, vol. 129:162-170 (2007).
Reetz, Manfred T. et al., "Iterative saturation mutagenesis (ISM) for rapid directed evolution of functional enzymes," Nature Protocols, vol. 2(4):891-903 (2007).

(Continued)

*Primary Examiner* — Jacob Cheu
(74) *Attorney, Agent, or Firm* — Nelson Mullins Riley & Scarborough LLP; Jane E. Remillard, Esq.; Jill Gorny Sloper, Esq.

(57) ABSTRACT

The invention is directed to a method of determining whether a non-purified sample contains a target protein bound to a ligand of interest comprising the steps of: a) exposing said non-purified sample to a temperature which is capable of causing or enhancing precipitation of the unbound target protein to a greater extent than it is capable of causing or enhancing precipitation of the target protein bound to said ligand; b) processing the product of step a) in order to separate soluble from insoluble protein; and c) analyzing either or both the soluble and insoluble protein fractions of step b) for the presence of target protein, wherein said target protein is not detected on the basis of enzymatic activity of a tag, peptide, polypeptide or protein fused thereto. Particularly, the invention may be used to determine whether drugs can bind to their protein targets in samples derived from patients to ascertain whether a certain drug can be used in a therapy for that patient. Additionally, the invention is directed to an instrument for use in the methods of the invention and use of a kit in the methods of the invention comprising an antibody and/ or a non-protein fusion tag.

18 Claims, 10 Drawing Sheets

(56) References Cited

OTHER PUBLICATIONS

Senisterra, Guillermo A. et al., "Application of High-Throughput Isothermal Denaturation to Assess Protein Stability and Screen for Ligands," Journal of Biomolecular Screening, vol. 13(5):337-342 (2008).

Song, Jae Kwang et al., "Enhancement of stability and activity of phospholipase A1 in organic solvents by directed evolution," Biochimica et Biophysica Acta, vol. 1547:370-378 (2001).

Vedadi, Masoud et al., "Chemical screening methods to identify ligands that promote protein stability, protein crystallization, and structure determination," PNAS, vol. 103(43):15835-15840 (2006).

West, Graham M. et al., "Mass Spectrometry-Based Thermal Shift Assay for Protein-Ligand Binding Analysis," Analytical Chemistry, vol. 62(13):5573-5581 (2010).

International Preliminary Report on Patentability for Application No. PCT/GB2012/050853, 4 pages, dated Jan. 22, 2013.

International Search Report and Written Opinion for Application No. PCT/GB2012/050853, 8 pages, dated Jun. 5, 2012.

Anderson, N. Leigh et al., "Analytical Techniques for Cell Fractions. XXIII. A Stable Thermal Gradient Device for Heat Denaturation Studies on Proteins," Analytical Biochemistry, vol. 91:441-445 (1978).

Anderson, N. Leigh et al., "The beta and gamma Cytoplasmic Actins are Differentially Thermostabilized by MgADP; gamma Actin Binds MgADP More Strongly," Biochemical and Biophysical Research Communications, vol. 89 (2):486-490 (1979).

\* cited by examiner

METHODS FOR DETERMINING LIGAND BINDING TO A TARGET PROTEIN USING A THERMAL SHIFT ASSAY

The present invention relates to methods of investigating protein ligand binding interactions, in particular through the use of thermal shift analysis.

More particularly, the invention relates to methods for determining ligand binding to a non-purified target protein comprising steps of heating the non-purified target protein and ligand and analysing the product to detect soluble target protein. In certain embodiments, the methods of the invention use a separation step to separate soluble from insoluble proteins after heat treatment to estimate the amount of soluble target protein and thus thermally stable ligand bound target protein. The invention also relates to an instrument for use in the methods comprising a heating means, a means for separating soluble from insoluble protein and a means for analysing soluble or insoluble protein for the presence of target protein. The use of a kit comprising an antibody or a non-protein fusion tag in the methods of the invention is also described.

The detection of ligand binding to proteins is important in many different areas of biology and medicine. Particularly, during the development of chemical compounds into drugs, it is important to know if the compound interacts with the drug target. The monitoring of target protein-ligand interactions can therefore be used in initial screening for interacting ligands from large chemical libraries, as well as during optimization of an initial ligand into a candidate drug. Further, it is important to understand the interaction of a drug with other proteins (so called "off target interactions") where such interactions may result in side effects of treatments.

In other medical applications, it is important to determine whether a particular drug is able to bind its target protein in a patient or an animal model (for the disease). For a drug to be efficient, it needs to be absorbed in the stomach/gut (or if injected, it should enter the blood) and be transported to the right location in the body. If the drug is not targeted to an extracellular protein or receptor, the drug also needs to be transported into the cell in order to allow it to access the target protein. During all these transport processes, the drug needs to be stable and to avoid excretion from the kidney and degradation, e.g. in the liver or by cellular metabolic enzymes. The drug further needs to survive cellular drug resistance processes, such as degradation by P450 enzymes or translocation by multi-drug efflux channels. Finally, the drug needs to be able to bind to the drug target protein. Drug resistance in cancer and infection therapy is sometimes due to subtle mutations in the region of the drug-binding site on the target proteins. However, in the path from drug to target, drugs will meet many different environments of the body and can potentially interact with many different proteins along the way.

The high complexity of the path for the drug before it reaches the binding site on the target protein is probably one reason why current predictive methods based on clinical diagnostics, expression profiling and sequencing only have limited success in predicting therapeutic efficiency. A potential means for measuring whether a drug has reached its target is to perform direct measurement of the drug-target protein interaction in the target cells of the body. Although this would not measure events downstream of the drug target, it would integrate all steps from drug to target as described above. Such measurements may therefore encompass many of the critical steps of therapeutic efficiency and would be a valuable predictor of the efficiency of many drugs and therefore as a clinical diagnostic tool. Thus, it is desirable to be able to detect ligand-protein interactions in non-purified samples e.g. those from patients, to study drug interactions and efficiencies.

Thermal shift assays have been developed in the art which can assess protein-ligand binding where the protein is in purified form. These assays have been developed on the basis of two principles, namely that a purified protein will melt and unfold at a particular temperature and that the binding of a ligand to a protein will thermally stabilise the protein. Thus, the binding of a ligand to a protein can be detected on the basis that the purified protein will show an increase in thermal stability once a ligand is bound and hence the protein will melt at a higher temperature once ligand is bound than purified protein alone. Vedadi et al (PNAS, 103(43), 15835-15840, 2006) evaluated chemical screening methods to identify ligands that promote protein stability, crystallisation and structure determination. In these methods, the thermal stability of recombinant purified proteins was assessed after screening against small molecule libraries. An increase in protein thermal stability and thus ligand binding was measured using either fluorimetry (where fluorescent probes were used) or static light scattering. However, as discussed above, this method used purified proteins which melted at a particular temperature (as determined by a reference sample using unligated protein) allowing an increase in stability at the melting temperature to be measured.

Moreau et al (Mol. BioSyst., 6, 1285-1292, 2010), recently used GFP as a reporter system to determine the stability of a target protein and its ligand-associated stabilisation, where GFP was fused to the target protein. However, this method is not ideal. Firstly, the method requires the construction and expressions of a fusion protein and can therefore not be used in natural cells and tissues but only in transformed cells. Further, the method can only be used to detect ligand binding to proteins which are less stable than GFP. Finally, the use of additives or salts affects the stability of GFP and thus a control GFP must be used for every experiment.

Thus, the thermal shift assays described in the prior art were only used in connection with purified protein, or in one case (Moreau et al, supra) in connection with a purified protein mixed with one other protein after purification where the protein is fused to GFP. In contrast to this, the inventors have developed an assay which can be used to determine binding of a ligand to a non-purified protein where the non-purified protein is not detected based on the enzymatic activity of any tag or peptide, polypeptide or protein fused thereto. Thus, the inventors have shown that it is possible for a non-purified protein e.g. in a cell, cell lysate or other complex liquid containing many different biomolecules, to unfold and precipitate with a characteristic temperature dependence, in a similar way to a purified protein. This discovery was unexpected since the conditions that are present in cells and in non-purified samples are quite different to the ones in a purified sample. Thus, in a non-purified sample or in a cell, it would be expected that several different processes may affect the solubility of a protein, which would act in parallel, such as different protein crowding effects or different chaperon or membrane interactions of partially unfolded proteins. The inventors used this finding as discussed above to develop a thermal shift assay, which can detect ligand binding to proteins in non-purified samples, based on the ability of non-purified proteins to melt at characteristic temperatures. The method is generic and can be used for most target protein and ligand combination, unlike the methods of the prior art. The assay investigates the thermal stability of the target protein in non-purified form at a particular temperature where an increase in thermal stability is indicative of ligand binding.

Thus, the thermal stability of the non-purified target protein with added ligand is compared to the thermal stability of the non-purified target protein without ligand. Any increase in thermal stability of the non-purified target protein plus ligand compared to non-purified target protein without ligand indicates that ligand is bound to the non-purified target protein. Particularly, any increase in thermal stability is determined by detecting whether or not the target protein is soluble after heat treatment. The assay of the invention therefore employs a simple step of separating soluble from insoluble proteins to identify any soluble target proteins. As discussed above such soluble proteins are associated with being thermally stable at the temperature applied to the sample and thus with having bound ligand. The separation step to discriminate between soluble and insoluble proteins thus allows the assay of the invention to be used to detect any target protein and therefore provides a generic method.

Therefore, in one aspect the invention provides a method for identifying a ligand which is capable of binding to a target protein wherein said target protein is non-purified comprising the steps of
(a) exposing a sample comprising said non-purified target protein and a test molecule, to a temperature which is capable of causing or enhancing precipitation of said target protein
(b) processing the product of step (a) in order to separate soluble from insoluble protein and
(c) analysing the soluble proteins of step (b) for the presence of target protein, wherein said target protein is not detected on the basis of enzymatic activity of a tag, peptide, polypeptide or protein fused thereto.

Thus, as discussed above, the method of the invention is concerned with detecting ligand binding to a target protein in a non-purified sample where surprisingly a target protein in such a sample is capable of melting or unfolding with a characteristic temperature. When a target protein is bound to a ligand, the thermal stability of the target protein is generally increased and thus the target protein may melt at a higher temperature when ligand is bound than when no ligand is present. Applying a temperature to a sample which usually melts/unfolds unbound target protein may therefore result in unbound target protein being unfolded and target protein to which a ligand is bound remaining folded to a larger extent. The detection of higher levels of folded target protein is therefore indicative of ligand binding. Folded target proteins are generally soluble whereas unfolded proteins are generally insoluble. Hence, the solubility of a protein is linked to its thermal stability. Thus, the detection of higher levels of soluble target protein after heat treatment using a temperature at which the target protein usually start to precipitate and become insoluble indicates the presence of folded target protein with an increased thermal stability and hence ligand binding.

The invention is concerned with analysis of impure samples. This allows the technology to be used in a "biosensor" type method. Non-purified samples, in particular clinical or environmental samples, which may contain a ligand of interest can be analysed by adding the target protein to the sample, either as a purified protein or in a non-purified sample (e.g. as a cell lysate). Such methods allow quantification of the presence of a drug or other analyte in a serum sample, even though the target protein is originally not present in the serum. A cell lysate containing the target protein, e.g. from the target cells of the drug can be added to the clinical sample.

Thus, the present invention provides a more general method of determining whether a non-purified sample contains a target protein bound to a ligand of interest comprising the steps of:
(a) exposing said non-purified sample to a temperature which is capable of causing or enhancing precipitation of the unbound target protein to a greater extent than it is capable of causing or enhancing precipitation of the target protein bound to said ligand;
(b) processing the product of step a) in order to separate soluble from insoluble protein; and
(c) analysing either or both the soluble and insoluble protein fractions of step b) for the presence of target protein, wherein said target protein is not detected on the basis of enzymatic activity of a tag, peptide, polypeptide or protein fused thereto.

The skilled man is familiar with thermal shift analysis of purified proteins and the melting point curves produced thereby. The midpoint of the melting point curve may be taken to be the melting point of the protein and this temperature can change on ligand binding. It is appreciated that depending on the nature of the shift caused by ligand binding, at certain temperatures there may be some melting (precipitation) of both bound and unbound proteins but that precipitation occurs to a greater extent with the unbound protein. The temperatures at which the shift is visible and the amount of precipitated protein differs are discriminatory temperatures and temperatures within that range can be used as a single discriminatory temperature according to step (a) above. That is particularly so when the m.p. of unbound and bound target proteins are known and the method is performed as an assay for the presence of target protein and/or ligand in the sample. Thus ligand may be added to a sample to confirm the presence of target protein.

The method of the invention is a generic method for determining ligand-target protein binding in a non-purified sample. Unless otherwise clear from the context, discussion herein of "non-purified protein" applies mutatis mutandis to 'non-purified samples'. This method has many advantages over the methods of the art. Firstly, it abrogates the need to purify proteins in order to investigate ligand binding. Further, the method does not require the recombinant expression of target protein or the production of a protein containing a fusion reporter protein (such as in Moreau et al, supra). It further allows the investigation of ligand binding in cell culture, animal or patient samples which was not previously possible using thermal shift binding assays. As discussed above, this is important for analysing whether a particular drug can be efficiently used to treat disease in a particular patient and to assist in determining optimal dosage of the drug. For example, this has important ramifications for the treatment of cancer and infectious diseases, where drug resistance often can occur. In such cases being able to detect patients who would not be effectively treated with the drug, allows other therapies to be commenced, or drug dosage to be adjusted.

Further, the detection steps of the method of the invention do not require the use of expensive equipment or machinery; indeed, the separation step can be achieved using a filter and target protein detected for example using antibodies. The method can be used for any protein to detect the binding of a ligand; there is no requirement to design specific probes etc for each protein to be detected in the method. Thus, the method of the invention represents an efficient, reliable way of determining protein-ligand binding in a non-purified sample. Additionally, as discussed further below, the method can be easily multiplexed and used to screen libraries of ligands or proteins for interaction.

The term "target protein" as used herein, refers to a protein which is being assessed in the method of the invention for ligand binding. The target protein can therefore be any protein which is present in a sample. The target protein may be naturally occurring e.g. in a cell or cell lysate or animal or patient sample or may be recombinantly expressed e.g. may be expressed from a plasmid which has been transformed into a cell. As mentioned above, the target protein may not initially be present in the sample but may be added thereto to investigate the presence of ligand in the starting sample. Thus, according to the present invention, the 'sample' is the test sample which is treated in step (a) and this may be different from the starting sample, e.g. the clinical sample. Likewise, ligand may be added to the starting sample. Additions of known amounts of target protein or ligand may assist in obtaining quantitative data.

The target protein may be in wildtype form i.e. as it usually occurs in nature or may comprise one or more mutations. Thus genes/cDNA/coding regions encoding a protein can be mutated to produce variants of that protein e.g. mutants with varying abilities to bind the ligand. As discussed further below, these mutants can be produced in an expression system wherein the variants, which for example have increased ligand binding, can be selected using the methods of the invention.

Typically, the target protein will have a native or native-like conformation and will be soluble. Native or native-like proteins are expressed in soluble form and/or correctly folded. Native-like membrane proteins do not have to be present free in solution, but may be present in cellular membranes or membrane vesicles rather than inclusion bodies. Thus native-like proteins are generally not insoluble, present in inclusion bodies, aggregated or misfolded.

The target protein may exist in the form of numerous variants across an animal population. These variants may exist within a healthy animal population, or the variation in the protein may lead to disease or drug resistance within a population. The methods of the invention provide a means of screening a ligand across a range of different target protein variants. Such information may be useful in order to develop ligands that bind to certain protein variants specifically, or to determine which form of therapy may be most adequate for a patient based on the protein variant which they naturally express. Thus, the method may be repeated with two or more target proteins, those target proteins being variants of the same protein.

A "soluble protein" can be defined in reference to possession of a native or native-like conformation. Further, a soluble protein can be described as a protein which remains in the supernatant after centrifugation of a sample (with a prior lysis step if said protein is within a cell. Centrifugation can typically be carried out between 100 g and 20000 g. The duration of centrifugation can be from 1 minute (typically at least 10 minutes) to at least 1 hour, where the duration required generally decreases as the centrifugal force increases. Particularly suitable conditions for providing only soluble proteins in the resultant supernatant include 30 minutes at 3000 g or 15 minutes at 20000 g.

The term "non-purified target protein" refers to the target protein when not in isolated form or alternatively viewed when present with other compounds e.g. proteins. The non-purified target protein to be used in the methods of the invention are in non-purified form before the addition of the test molecule (potential ligand) or in the absence of the test molecule. Thus, the non-purified target protein is present with compounds other than the test molecule (potential ligand) which is tested to determine whether or not it is a ligand for the target protein. The non-purified target protein thus includes target protein when comprised within or on cells, cell lysates and samples obtained directly from patients (human patients or animal patients or disease models e.g. dog, cat, monkey, rabbit, mouse, rat etc) such as tissue samples, blood, serum, plasma, lymph etc. The non-purified target protein includes target protein when comprised in one or more cell colonies, where a cell colony is defined as a circumscribed group of cells, normally derived from a single cell or small cluster of cells growing on a solid or semi-solid medium (i.e. culture media with the addition of 0.1% or greater agar). The non-purified target protein may also be comprised in a liquid culture of cells. A liquid culture of cells may comprise cells which have all originated from a single cell i.e. the cells within the liquid culture may be clonal, or the liquid culture may comprise a suspension of different cells. The cells of the colonies or in liquid culture may be prokaryotic i.e. bacteria or eukaryotic cells e.g. yeast, unicellular eukaryotes such as Leishmainia, insect cells or mammalian cells or cell lines. Cells in liquid culture or grown as colonies may be formed as *E. coli, Bacillus subtilis, Streptococcus lactis, Streptococcus lividens, Lactococcus lactis, Staphylococcus aureas, Aspergillus niger, Picia pastoris, Saccharomyces cerevisiae* or *Schizosaccaromyces pombe*. All of the above are examples of a sample comprising a target protein.

As mentioned above, key to the present invention is the finding that 'dirty' samples can yield reliable information when undergoing thermal shift analysis. Thus, the sample at (a) is non-purified but there may be circumstances where a purified target protein has been added to a dirty starting sample. The sample is not purified and contains components such as other proteins, cell debris, nucleic acids etc., as described herein in the context of "non purified target protein".

Typically, a non-purified target protein has not been subjected to a purification process which would result in the purification of the target protein. Such a purification process may comprise of several steps and thus the non-purified target protein used in the present invention has not been subjected to all such necessary steps to produce a purified protein. For example where the protein is present in a tissue, steps of extraction, precipitation and separation e.g. by centrifugation or chromatography may be used to purify the protein. The non-purified target protein of the present invention would not be subjected to all such steps and thus a purified target protein would not be isolated. It is possible that the non-purified target protein could have been subjected to one or more steps e.g. the extraction step of a purification process, as long as the purification process was not completed and a purified protein was not isolated. The non-purified target protein is therefore typically present with other compounds or proteins and thus the target protein is not present in isolated form.

The term "test molecule" as used herein refers to any molecule or compound, which is tested in the methods of the invention to determine whether or not it is a ligand for the target protein. Alternatively viewed, the test molecule is a potential ligand for the target protein. Thus, the test molecule or ligand may be a protein, polypeptide, peptide, RNA, or DNA molecule. In a particular embodiment, the molecule/ligand may be a drug or pharmaceutical product, a cell metabolite or a hormone e.g. in serum. The test molecule or ligand may be naturally occurring or may be synthetically or recombinantly produced, using any of the methods already described or discussed further below.

The test molecule used may or may not bind to the target protein; in one aspect the method of the invention determines or assesses whether a particular molecule or compound is capable of binding to the target protein i.e. whether a test molecule or compound is a ligand. Thus, the invention can be used to screen a small molecule library for molecules which are capable of binding to the target protein. Some of the molecules tested may not bind, whereas others may bind to the target protein. Additionally, the method of the invention can be used to identify variants of small molecules known to bind to the target protein, which can bind the target protein with higher affinity (or alternatively with lower affinity) where this is often reflected in the degree of thermal stabilization. Thus, test molecules can be mutated ligands or known (or unknown) target protein binding partners. The production of such mutated molecules is achieved by using any of the mutation processes described herein.

Thus, in one aspect, the present invention provides a method for identifying a ligand capable of binding to a target protein comprising the steps of:
(a) exposing a non-purified sample comprising said target protein and a test molecule to a series of different temperatures, including a temperature which is equal to or greater than the initial melting temperature of the target protein;
(b) processing the products of step a) in order to separate soluble from insoluble protein and
(c) analysing either or both the soluble and insoluble protein fractions of step b) for the presence of target protein, wherein said target protein is not detected on the basis of enzymatic activity of a tag, peptide, polypeptide or protein fused thereto.

The term "ligand" as used herein refers to a test molecule or more generally to a compound which is capable of binding to the target protein. A target protein may have a co-factor or physiological substrate bound thereto but methods of the invention investigate the melting point of a target protein bound to a ligand of interest as compared to the target protein when not bound to that ligand (unbound target protein). The ligand of interest may bind elsewhere on the protein or may compete for binding e.g. with a physiological ligand. Ligands of interest may be drugs or drug candidates or naturally occurring binding partners, physiological substrates etc. Thus, the ligand can bind to the target protein to form a larger complex. The ligand can bind to the target protein with any affinity i.e. with high or low affinity. Generally, a ligand which binds to the target protein with high affinity may result in a more thermally stable target protein compared to a ligand which binds to the target proteins with a lower affinity. Typically, a ligand capable of binding to a target protein may result in the thermal stabilisation of that target protein by at least 0.25 or 0.5° C. and preferably at least 1, 1.5 or 2° C.

Hence, when a test molecule is already known to bind the target protein (and thus is a ligand for the target protein), the method of the invention can be used to assess the binding of the ligand to the target protein e.g. to determine the strength of the interaction. In this aspect, the invention provides a method for assessing ligand binding to a target protein wherein said target protein is non-purified comprising the steps of a) exposing a sample comprising said target protein and said ligand, to a temperature which is capable of causing or enhancing precipitation of said target protein, b) processing the product of step a) in order to separate soluble from insoluble protein and c) analysing the soluble proteins of step b) for the presence of target protein wherein said target protein is not detected on the basis of enzymatic activity of a tag, peptide, polypeptide or protein fused thereto.

In order to assess or determine ligand binding to a non-purified target protein or to identify a ligand for a non-purified target protein, the test molecule or ligand is typically added to the sample. However, it is possible that the test molecule or ligand is already present in a sample comprising the non-purified target protein e.g. is naturally occurring. Thus the invention may also provide a method for identifying a ligand which is capable of binding to a target protein wherein said target protein is non-purified comprising the steps of
(ai) adding a test molecule to said non-purified target protein
(a) exposing the product of step (ai) to a temperature which is capable of causing or enhancing precipitation of said target protein
(b) processing the product of step (a) in order to separate soluble from insoluble proteins and
(c) analysing the soluble proteins of step (b) for the presence of target protein wherein the presence of the target protein indicates that said molecule is bound to said target protein and is a ligand capable of binding to said target protein and wherein said target protein is not detected on the basis of enzymatic activity of a tag, peptide, polypeptide or protein fused thereto.

Typically, where the test molecule (potential ligand) is present extracellularly e.g. in solution, this may be simply added to the non-purified target protein e.g. mixed together with the non-purified target protein where this is also in solution or dropped onto the target protein e.g. where the target protein is present in an aliquot of harvested cells. Alternatively, the test molecule (potential ligand) may be expressed recombinantly from a vector encoding the test molecule. The step of adding the test molecule may therefore involve transforming or transfecting a cellular sample with the vector encoding the test molecule and/or inducing expression of the test molecule from the vector in a cellular sample once transformation or transfection has been carried out. The step of adding the test molecule further includes inducing expression of a test molecule encoded by a gene naturally occurring in a cellular sample.

Further, where the target protein is present within a cell, the method may require an extracellular test molecule or ligand to be transported into the cell to contact the target protein. For test molecules or ligands which bind to a target protein on the cell surface however, there is no need for transport into the cell. Alternatively, or additionally, where the target protein is present in a cell (or on the cell surface), a step of lysis may be carried out before, simultaneously or after the test molecule or ligand has been added. Such a lysis step allows contact between the target protein and the test molecule or ligand and/or the later assessment of any binding between the test molecule or ligand and target protein. Thus, any necessary lysis step is generally carried out before the separation step of the method of the invention. It will be apparent that a step of lysis may only need to be carried out on samples where the target protein is comprised within a cell. The lysis step may be thermal dependent i.e. the lysis may only occur at a particular temperature e.g. at the end of a thermal cycle.

The lysis step of the present invention will have different requirements depending on whether the cells are subjected to heat treatment before or after any lysis step. For cells subjected to lysis before heat treatment, preferably, the lysis step is non-denaturing, allowing target proteins to retain a native i.e. correctly folded or native-like conformation. This is referred to herein as native lysis. This can be carried out chemically or otherwise using reagents which are well known in the art e.g. urea, lyzozyme containing buffers or detergents. The degree of lysis must be sufficient to allow proteins of the cell to pass freely out of the cell. Typically, when dealing with membrane bound proteins, lysis is performed in the presence of detergents or amphiphiles, for example Triton X-100 or dodecylmaltoside, to release the protein from the membrane. The lysis step can alternatively be carried out by freeze thawing the cells or colonies. More preferably, lysis is carried out using both native lysis buffer and freeze thawing the cells. Preferably, the lysis buffer contains lysozyme, for examples at 50-750 μg/ml, more preferably at 100-200 μg/ml. DNAse can also be found in native lysis buffer preferably at 250-750 μg/ml. Native lysis buffer may contain for example 20 mM Tris, pH 8, 100 mM NaCl, lysozyme (200 μg/ml) and DNAse I (750 μg/ml). For target proteins known to be inserted into cellular membranes, detergents would be added to the lysis buffer at typical concentrations where they are known to solubilise membrane-inserted proteins in a native form, such as 1% n-dodecyl-β-maltoside. Typically, the cells will be exposed to the lysis buffer for 15-60 minutes, preferably around 30 minutes. The step of freeze thawing is preferably repeated, i.e. two or more cycles, preferably 3 or more cycles of freeze thawing are performed. In one preferred embodiment lysis is achieved by a 30 minute incubation at room temperature with lysis buffer and three ×10 minutes freeze thawing.

Typically, the percentage of cells lysed within a sample (e.g. a cell colony or cell culture) during the lysis step is 5-100%. Thus, it is not necessary when performing a step of lysis for all cells within a sample to be lysed. Only a small percentage are required to be lysed in order to release sufficient target protein to either contact with ligand and/or to be subjected to the separation step.

As discussed briefly above, it is possible that the test molecule or ligand is already present in a sample comprising the target protein. In this instance it may be possible to investigate natural ligand binding to a target protein e.g. by diluting the sample with buffer and detecting any negative shift in thermal stability of the target protein when a ligand is released.

The methods of the invention require that the non-purified sample is exposed to "a temperature which is capable of causing or enhancing precipitation of said target protein". This refers to a temperature which is capable of causing or enhancing precipitation of target protein in the absence of the test molecule (potential ligand). Likewise the non-purified sample is exposed to "a temperature which is capable of causing or enhancing precipitation of the unbound target protein to a greater extent than it is capable of causing or enhancing precipitation of the target protein bound to said ligand". "Unbound" refers to the target protein when not bound to, i.e. in the absence of, the ligand of interest.

Thus, as discussed previously, the inventors have found that proteins in non-purified form generally precipitate with a particular temperature dependence, (i.e. having distinct melting temperatures) in a similar manner to purified proteins, despite the varying conditions found within non-purified samples and particularly within cells. Therefore, the protein may precipitate over a small temperature range. Occasionally, some proteins may undergo several transitions in their state during heating over a temperature range indicating that there are several forms of the protein present in the sample (e.g. different spliced forms, phosphorylated forms, or bound to other proteins). In this situation, it is possible that a test molecule/ligand will not bind to all forms of the protein in all transition states. Hence, a test molecule or ligand may only bind protein in one or more of its transition states. Thus, it is possible that a test molecule/ligand may only be able to thermally stabilise certain transition states or forms of the protein and thermal shifts in the stability will only be seen for these transition states.

Where a target protein precipitates over a small temperature range, the initial melting temperature is the first temperature in the range and the final melting temperature is the last temperature in the range. Thus, the initial melting temperature is the lowest temperature at which target protein begins to precipitate e.g. at least 5% of the target protein is precipitated and the final melting temperature is the first temperature at which no soluble target protein is detected. e.g. less than 5% of target protein is in soluble form. Typically, at least 95% of target protein is melted and precipitated.

Therefore, when a target protein precipitates over a temperature range, the target protein may begin to precipitate or unfold at a particular temperature at which point the amount of soluble target protein present will begin to decrease and the amount of insoluble target protein present will increase (since thermal stability is linked to solubility). Therefore, some soluble protein may still be detectable at the initial melting temperature until a slightly higher temperature is applied, at which point little or no soluble protein is detectable.

The final melting temperature for a protein is therefore a particular temperature at which there is a significant decrease of soluble protein detected, typically at least 95% of the protein is insoluble. For problematic proteins having multiple transitions, each of these transitions may result in a smaller amount of protein becoming insoluble, but this would still be significant enough to be measured (e.g. at least 10% of the protein becomes soluble at each transition). Where the protein precipitates over a small temperature range, where the percentage of soluble protein decreases until no soluble protein is detectable and thus the protein is completely unfolded or precipitated, an initial and final melting temperature can be determined. Hence, at the initial melting temperature of such a temperature range i.e. the lowest temperature at which target protein begins to melt or precipitate, at least 5, 10, 15, 20, 25, 30, 35, 40, 45, 50, 55, 60, 65, 70, 75, 80, 85, 90 or 95% of the target protein may melt or precipitate. Alternatively viewed, at the initial melting temperature of a temperature range, the amount of soluble target protein detected decreases by at least 5, 10, 15, 20, 25, 30, 35, 40, 45, 50, 55, 60, 65, 70, 75, 80, 85, 90 or 95%. Further, the amount of insoluble target protein present may increase by at least 5, 10, 15, 20, 25, 30, 35, 40, 45, 50, 55, 60, 65, 70, 75, 80, 85, 90 or 95%.

It is also possible that a target protein may unfold and precipitate at one specific temperature. In this instance, preferably at least 95% of the target protein will be in insoluble form at a specific temperature and hence the protein may not precipitate over a small temperature range. The initial melting temperature for such proteins may therefore be close to the final melting temperature.

The temperature which can be applied in the present invention may be any temperature from the initial melting temperature at which the target protein begins to unfold. Any temperature equal to or higher than the initial melting temperature will be capable of causing or enhancing precipitation of the target protein. Thus, a target protein with a higher thermal stability due to ligand binding will generally not unfold or precipitate at this temperature and a higher amount of soluble protein will be detected as compared to target protein alone which has either completely unfolded or begun to unfold. The temperature is thus discriminatory, causing or enhancing precipitation of the unbound target protein to a greater extent than it causes or enhances precipitation of the target protein bound to the ligand of interest.

The detection of an increased amount of soluble target protein at a particular temperature when a test molecule is present as compared to the amount of soluble target protein present when the test molecule is absent is indicative that the molecule is a ligand for the target protein and that the test molecule is bound to the target protein. Where the temperature used in the present invention is the initial melting temperature or a temperature between the initial melting temperature and the final melting temperature (i.e. not a temperature which results in at least 95% of the target protein being insoluble (the final melting temperature or a higher temperature than this)) it may be necessary to carry out a control reaction simultaneously for target protein without ligand present, in order to compare the amounts of soluble protein detected in both cases, to detect the samples with ligand where an increased amount of soluble target protein is present compared target protein alone. This is typically done by measuring the melting curve of the protein in similar non non-purified samples. However, where a temperature is used in the invention at which no or very little soluble target protein is detected (i.e. target protein without ligand) e.g. the final melting temperature, there is no need to use a comparison or control for every measurement. In this case, any detection of soluble protein in the method indicates the presence of a thermally stable and hence ligand bound target protein. Such a temperature would typically be equal to or higher than the final melting temperature.

Additionally, the temperature can be chosen in the present invention to screen for only ligands which bind to the target protein with a high affinity. Thus, typically the higher the temperature at which soluble proteins and hence thermally stable ligand bound target proteins are detected, the higher the affinity of the ligand binding to the target protein is likely to be. Hence, if only high affinity interactions are required to be detected, a temperature which is higher than the final melting temperature can be selected e.g. 3, 4, 5, 6, 7, 8, 9, 10 or more ° C. higher than the final melting temperature. Thus, preferably, the temperature selected would be higher than the final melting temperature of a temperature range. Alternatively, if it is desired to identify all molecules/ligands bound to the target protein, a lower temperature can be used, for example one equal to the initial melting temperature of a range. Alternatively viewed, when selecting for high affinity interactions, the discriminatory temperature of step (a) will be one which causes or enhances precipitation of unbound target protein to a much greater extent than it causes or enhances precipitation of the ligand bound target protein, e.g. at least 30% more, preferably at least 50% more, more preferably at least 60, 70 or 80% more.

The binding affinity of the ligand to the target protein can be determined through performing the method steps described above at a range of varying ligand concentrations or target protein concentrations. In such methods, the sample treated in step (a) will have added thereto a known amount of target protein or ligand. One can plot a dose-response curve, and therefore determine the binding constant of the ligand (i.e. the concentration of ligand or target protein at which half of the target protein is bound to ligand). Such binding information obtained in a clinical, impure sample would provide a more accurate interpretation of the binding characteristics of the ligand to the target protein under physiological conditions compared to information derived from pure samples. Such information could have useful applications to set dosing regimes for patients or to find a therapeutic window for a drug by studies of apparent binding constants in different organs of the body. Thus, certain aspects of the invention may also comprise a further step:

d) repeating steps a) to c) with one or more (e.g. 2 or more, preferably 3 or 4 or more) different concentrations of ligand or target protein.

The heating step can be carried out using any heat source which can heat a sample to a particular temperature. Thus, where the non-purified target protein and test molecule (potential ligand) are in liquid form, then preferably the heating step may be carried out in a PCR machine. However, incubators, waterbaths etc may also be used. Where the target protein is in a cell colony, an incubator is preferably used to carry out the heating step.

The invention further encompasses applying a range of temperatures to the target protein and test molecule and processing and analysing the target protein after incubation at each temperature in order to produce a precipitation curve for each target protein and test molecule combination. Thus, a target protein and ligand may be incubated at any temperature range as long as one temperature is used which is capable of causing or enhancing precipitation of the target protein (i.e. without bound ligand). Preferably therefore, the temperature range applied includes incubating at the initial melting temperature or at a temperature higher than the initial melting temperature. By incubating the non-purified target protein and test molecule at a whole range of temperatures, it is possible to determine the temperature at which the target protein precipitates when ligand is bound. Further, if a control of non-purified sample without ligand is subjected to the same temperature incubations, it is possible to identify ligand bound protein samples without prior knowledge of the target protein melting temperature. Preferably, any such heating of a control would be carried out simultaneously to the heating of the non-purified sample and test molecule/ligand. By using a precipitation curve, it is also possible to determine ligands which have the greatest effect on thermal stability when more than one ligand is being investigated.

Typically a temperature range may be used to produce a precipitation curve where the temperatures used are about 2, 3, 4, 5, 6, 7, 8, 9 or 10° C. different from one another. Thus the target protein and test molecule could be incubated at any one of more of 27, 30, 33, 36, 39, 42, 45, 48, 51, 54, 57, 60, 63, 66, 69, 72 and 75° C. as long as one of the temperatures is equal to or higher than the initial melting temperature for the target protein. Where the target protein and test molecule are heated over a temperature range, this can be carried out in a PCR machine where an initial temperature can be set and then increased by the desired amount after a particular amount of time e.g. 1, 2, 3, 4 or 5 minutes. As discussed previously, a small aliquot or amount of sample (e.g. 1 or 2 µl) can be removed after heating at each temperature in order that the solubility of the target protein can be analysed. Where the non-purified target protein is present in one or more cell colonies, a portion of the colony may be lifted off after each incubation e.g. by placing filter paper on the top of the colony.

In order to apply the method of the invention, it is necessary to determine the melting temperature(s) of the target protein of interest without test molecule/ligand so that any thermal shift in the presence of test molecule/ligand can be detected. Thus, the melting temperature(s) of the target protein can be determined before the method of the invention is carried out or a simultaneous control reaction can be carried out with the method of the invention where a range of temperatures are applied to the control and to the target protein and molecule e.g. as discussed above to produce a precipitation curve. The Tms (temperature at which 50% of protein is precipitated) of many target proteins in purified samples are also known in the art and although the Tms for non-purified target proteins are slightly different, these can often be used as a guide for the melting temperatures of non-purified proteins.

"A temperature capable of causing or enhancing precipitation" of target protein therefore refers to a temperature or a temperature range as discussed above at which there is an increase in the precipitation or alternatively viewed the unfolding or melting of a target protein as compared to target protein at a lower temperature. The temperature is generally an increased temperature compared to the temperature at which the target protein is usually found e.g. 37° C. for target proteins within a patient. Thus the temperature applied is typically above 37° C., preferably above 40° C., e.g. above 50° C.

The temperature used in the invention thus preferably causes an increase in precipitation of the target protein by at least 5, 10, 15, 20, 30, 40, 50, 60, 70, 80, 90 or 95%. An increase in protein precipitation usually results in insoluble protein being produced and thus alternatively viewed, the temperature used in the invention may cause an increase in the amount of insoluble target protein present e.g. an increase of at least 5, 10, 15, 20, 25, 30, 35, 40, 50, 60, 70, 80, 90 or 95%. In the present invention, any enhancement of precipitation may be measured by measuring a decrease or reduction in the amount of soluble target protein present e.g. a reduction of at least 5, 10, 15, 20, 25, 30, 35, 40, 50, 60, 70, 80, 90 or 95%. Measurement of this decrease could for example be done using dot-blots or ELISA-experiment where the amount of bound antibody can be quantified using e.g. integration of fluorescence signals of florescence labelled antibodies.

The method of the invention further requires the use of a separation step (b) to separate soluble from insoluble proteins. The separation step can involve any separation method which is capable of separating soluble from insoluble protein. For example, a step of centrifugation can be used as described above or in a preferred embodiment, a step of filtration may be used. Thus, a filter can be used to separate soluble from insoluble proteins where soluble proteins will pass through a filter. Standard filter membranes can be used for filtering heated samples where the filters will typically have a pore size from 0.015 μm to 12 μm, preferably from 0.35 to 1.2 μm, more preferably from 0.45 μm to 0.8 μm. Preferably the filters have pore sizes below 4.0 μm, typically below 2.0 μm, more preferably below 1.0 μm. When the target protein is produced or expressed in cells, such as bacteria e.g. *E. coli*, an optimal pore size may be 0.1-1.5 μm. Where is target protein is from a eukaryotic cell or sample, preferred pore sizes may be larger. It will be appreciated that filters are manufactured and marketed as having a particular pore size but the manufacturing process may occasionally result in a few smaller or larger pores; the sizes listed, which refer to the diameter, are thus the most common pore size of a given filter. Although reference is made to a range of potential pore sizes, any single filter will usually have one designated pore size e.g. 0.45 μm. Suitable filters are Super and GH polypro (from Pall) and Nucleopore (From Whatman).

It will be appreciated that target proteins from eukaryotic and prokaryotic samples and from different cell types may require the use of filters with different pore sizes. Selection of a suitable filter is well within the competency of someone skilled in this field. For example, it is possible to select an appropriate pore size, by using a set of test proteins for the desired cell type or sample and investigating their behaviour with filters of varying pore sizes.

As discussed previously, where the target protein is present within a cell, a step of cell lysis may be carried out prior to the separation step. Cell lysis will also be required when the sample is a cell sample and target protein is added thereto in order to assay for the presence of a ligand. When the present method is carried out on cell colonies, the lysis may be carried out directly on those colonies i.e. there is no need to pick the colonies and grow them in liquid culture (although this can be done). In this instance, it is preferred that the separation step is one of filtration. Further, where the method is performed on cell colonies, preferably, the filter paper is overlayed on the colonies to lift the colonies from the semi-solid or solid growth media. Alternatively, filters could be placed on the growth media and cells seeded directly onto the filter, the filter could then simply be lifted off with the colonies already on it. Preferably, the lifting of the colonies in this way can be carried out prior to the lysis step. As indicated above, the lysis can be carried out directly on the colonies on a filter. The filter with colonies attached can be treated with lysis buffer or overlaid on other membranes/filters treated with lysis buffer.

Filtration can also be carried out for liquid cultures of cells e.g. liquid cultures growing in a multi well plate e.g. a 96 well plate.

Filtration is carried out after any necessary lysis step is performed. It will be appreciated however that filtration and lysis may occur simultaneously when considering a whole colony since some cells may undergo lysis before others and hence may be filtered before or at the same time as others are lysed.

Preferably, where the separation step is filtration, proteins which pass through the filter are held on a solid support, e.g. a capture membrane, to allow screening/detection of the target protein(s) and then to allow the identification of sample(s) containing the target protein bound to ligand. Such capture membranes may typically comprise nitrocellulose. However, it will be appreciated that it is the first filter that separates soluble from insoluble protein in this method. In a preferred embodiment, proteins can simply be allowed to pass through the filter, possibly as a result of capillary action. In another embodiment, force may be applied vertically on the filter paper, wherein such forces can include the application of pressure or vacuum.

The capture membrane can fix the soluble proteins from the individual sample(s) and in this way, it is possible to multiplex this method. Thus, the positions of the target protein(s) on the capture membrane can be compared to the filter which either carries the original cell colonies, if the method is being carried out on cell colonies, or the sample spots. Thus, from the filtration blot, it is possible to track back and identify the original samples comprising the target protein and bound ligand. To aid in the process of identifying colonies comprising target protein bound to ligand, positive controls can be used. These are clearly seen on the final colony filtration blots and can enable the membrane/blot to be correctly orientated with the original colonies. Hence, after any filtration step is carried out, a solid support such as a capture membrane allows the ready identification of samples having target protein bound to ligand.

In another embodiment, the filter with heat treated sample(s) can be placed sample side down and a (nitrocellulose) capture membrane can then be placed on top of the filter and several layers of filter paper (and paper towels) can be placed on top of this. Force can then be applied to the top of this "sandwich" and ideally transfer buffer poured around the bottom to facilitate filtration and transfer of proteins onto the capture membrane.

In another embodiment, the filter is placed sample side up onto a capture membrane and a vacuum is applied to "pull" protein through the filter paper and onto the capture membrane.

Alternatively to filtration and centrifugation, affinity capture of soluble protein can be carried out. Many antibodies and affinity reagents that recognise the folded structure of the protein will bind the soluble protein with much higher affinity than the unfolded and precipitated protein. Also the recognition of smaller tags such as poly-Histidine tags binding to metal conjugates will often correlate with solubility when these tags are less accessible in the precipitated protein. Antibodies, metal conjugates and other affinity reagents can be linked to magnetic beads or column resin which is mixed with the heat treated non-purified sample. This mix can in a subsequent step be put in an appropriate valve and washed to remove insoluble protein when this does not have high affinity to the affinity reagent. The amount of protein bound to the affinity reagent, can subsequently be measured using for example Bradford techniques. gel electrophoresis, Elisa or surface plasmon resonance detection.

According to the methods of the invention it is possible to analyse either (or both) the insoluble or soluble fractions for the presence of target protein. The insoluble fraction is preferably solubilised prior to analysis, for example, as described in Example 3, the precipitated proteins may be dissolved in loading buffer prior to application to the separation gels. Preferably the methods of the invention involve a step (c) of analysing the soluble proteins for the presence of target protein. Thus, the soluble proteins obtained after the step of separation are preferably analysed for the presence of target protein. Hence, if a centrifugation separation step was carried out, the supernatant can be analysed for the presence of target protein and where a filtration separation step was carried out, the proteins which pass through the filter i.e. the filtrate can be analysed for the presence of target protein.

The target protein can be detected by various different methods. Thus, target proteins can be detected using various tags which are well known in the art, e.g. histidine tag, VS tag, T7 tag, FLAG tag or any short protein sequence to which a specific antibody is available, thioredoxin and maltose binding protein. Tags are preferably between 1-100 amino acids in length, preferably between 1-70, 2-50, 1-30 or 1-20 amino acids in length. More preferably, tags can be 3, 4, 5, 6, 7, 8, 9 or 10 amino acids in length. However, the target protein is not detected on the basis of any enzymatic activity of a tag, peptide, polypeptide or protein which is fused to the target protein. Thus, target proteins are not detected using an enzymatic activity exhibited by any such tags or proteins fused to the target protein, e.g. where the enzymatic activity results in the production of a detectable signal. For example, fusion tags that possess enzymatic activity such as green fluorescent protein, horseradish peroxidase, luciferase and glutathione-S-transferase are not used in the present invention to detect the target protein. Thus, although it is possible for any tag/protein to be fused to the target protein, the target protein is not detected using the enzymatic activity possessed by any such tags or proteins. Thus, in the case of a GFP tag, fluorescent green light is produced by an enzymatic reaction and hence it is specifically excluded in the present invention, for a target protein to be detected using such a reaction. Hence, the detection of the target protein by fluorescence produced from a GFP tag is excluded, since such fluorescence is the result of enzymatic activity possessed by the tag. Further, in a preferred embodiment, the target protein of the invention is not fused to a reporter protein with enzymatic activity. In a particularly preferred embodiment, the target protein is not fused to GFP. Thus, alternatively viewed, it is preferred that any tag fused to the target protein is a non-protein tag.

For a tag to be fused to the target protein, it is generally transcribed and translated with the target protein as a single molecule. Thus, antibodies which bind to the target protein and which may be labelled with HRP etc are not considered to be fused to the target protein. In such cases, the target protein may be detected using the HRP tag since this is not part of a fusion molecule with the target protein.

Thus, tags can be attached to a target protein by expressing such proteins as fusion proteins. As such, short tags are preferred, to allow proteins of interest to maintain a native-like conformation. Further, C-terminal tags are preferred, although N-terminal His tags are also used. It will be appreciated that a detection step involving the use of a tag fused to a target protein can only be used where the target protein is derived from a recombinant expression system. Therefore, generally this detection method will not be used when the target protein is for example obtained from a patient.

Target proteins can further be detected via fusion tags which act as the substrate in enzymatic detection methods, His tags being particularly suitable in this regard. For example, INDIA His Probe-HRP (Pierre, Rockford Ill., USA) can be used for detection wherein the target protein is either poly-histidine tagged or is histidine rich and where the target protein is detected by Nickel activated derivative of horseradish peroxidase which binds to His tags. Target proteins may also be detected on the basis of their own enzymatic activity.

Detection may alternatively be based on affinity binding between the target protein and a detection moiety or between a tag fused to the target protein and a detection moiety, for example an antibody, antibody fragment or affibody (non Ab based protein binding partner). Preferably, target proteins may be detected using antibodies, monoclonal or polyclonal, either directed to a tag or directly to the target protein (expressed on its own or as a fusion). Antibodies which are directed to the target protein are typically used to detect a target protein from a patient sample. Such methods allow for rapid and reliable analysis of a wide variety of target proteins, including those which themselves possess no catalytic activity. Target protein can also be detected using semi quantitative mass spectrometry (MS). In a fourier transform ion cyclotron resonance experiment using an orbitrap instrument typically 1000-2000 proteins can be detected simultaneously in a sample from a lysate. In a preferred embodiment a temperature scan of cells followed by lysis, filtration and in a final step the detection of all remaining soluble protein using mass spectrometry, at each temperature of the scan, allows precipitation curves to be measured in parallel for many proteins. This global proteome melting curve analysis could for example be used to detect so called off target effects of drugs, i.e. to monitor which other proteins in the cell appear to bind the drug. This global proteome melting curve analysis could also be used when searching for drug targets for drugs or drug candidates for which the drug target is unknown. For example, compound library screening direct on cells can identify compounds that generate preferred phenotypes in these cells indicative that the compound effects processes in the cell that are useful as drug targets for a certain disease. However, it is normally very challenging to identify with which protein or proteins in the cell the drug candidate interact. The global proteome melting curve analysis for thermal shift changes allow this to be performed for the proteins which are available at sufficient level to be detectable with MS.

Molecule/ligand binding to target proteins can be investigated in a recombinant expression system. Thus, genes/cDNAs/coding regions for the target protein can be transformed or transfected into expression systems in vectors/constructs, such as plasmids, viral vectors, cosmids and YACS. Such vectors may contain regulatory sequences and other elements well known in the art. For example, the gene/cDNA/coding region may be placed under the control of a promoter in a vector. Promoters used are generally capable of expressing the target protein within a particular host. In a specific embodiment, the promoter used is inducible i.e. the expression of the target protein can be controlled. Such inducible promoters/systems include lac wherein induction of expression is controlled by the addition of IPTG and tet on/off, wherein the induction of expression is controlled by the presence/absence of tetracycline and others are known in the field.

As described previously, the method of the invention may be used to screen libraries of small molecules for those which will bind to a target protein. In a preferred embodiment, this is carried out using multi-well plates where each compound of the library is added to an aliquot of cells, or a cell lysate. Alternatively libraries of mutant target protein may be screened to determine a mutant target protein which shows altered binding to a particular ligand. For example, mutant target proteins can be identified which have a closer or tighter association with a ligand than wildtype target protein. Where mutant target proteins are being assessed, measurements of the stability of the protein without ligand are desirable to decide whether the stabilisation is due to the ligand interaction or due to the mutant itself being more stable i.e. the mutation having a stabilising effect on the mutant protein. If the ligand is another protein, the stability measurement could instead be carried out on this non-mutant protein, where mutated protein variant can be selected which stabilises the non-mutated protein. This could, for example, be used to mature binding proteins (i.e. the ligands) such as, for example, antibodies, FAB-fragments, single chain antibodies or affibodies where random mutations are added to the binding protein and variants with apparent improved binding are detected by measuring improved stabilization of the non-mutated protein. In such a way, higher affinity binders could be selected from lower affinity binders. When binding proteins can serve as protein drugs targeted against e.g. specific receptors or cytokines, the method could be used to improve the affinity of such binders to the drug target of the protein drug.

Many different methods of mutagenesis are known in the art which could be employed to create a variant of the target protein or a library of variants of target protein. Possible procedures include truncation of the sequence, use of an exonuclease enzyme, introduction of a randomized site mutations using e.g. error prone PCR, introduction of randomised cassette or site-directed mutagenesis. For truncations, the number of nucleotides removed may be less than 2000, preferably less than 1000 and more preferably less than 800. Introduction of a randomised cassette for mutagenesis preferably uses a cassette containing less than 100 nucleotides.

Mutagenesis may be carried out on several copies of a nucleic acid sequence encoding the target protein so that a set of different mutated sequences can be screened, hence increasing the probability of identifying a target protein variant with the desired ligand binding properties. The use of random mutagenesis is especially preferred where there is no prior knowledge of which particular mutations may yield a variant which for example binds to the ligand more tightly i.e. has a higher affinity for the ligand.

Libraries of proteins can be created where the coding region has been randomly mutagenised and where different length constructs have been generated by erase-a-base or random priming reactions.

Thus, the methods of the present invention can be used to detect target protein variants which have altered and preferably have increased or higher affinity binding to a ligand. Additionally, the methods of the invention can be used to determine whether a target protein in a cell culture or patient sample will interact with a particular test molecule e.g. a drug. Hence, a preferred use of the method is to determine drug-protein interactions in cell culture during the drug development cycle to confirm that the drug binds to the target protein in this cell type. Similarly the method can be used to monitor drug binding to non-desired proteins, so called off-target binding. Another preferred use of the method is to determine drug-protein interactions in patient samples (e.g. tissue, blood, lymph etc), to provide an indication as to whether a particular drug therapy will be effective for that patient. If a tissue sample is to be examined, then the method of the invention may also incorporate a step of extracting a target protein from the tissue. Additionally or alternatively, a step of lysis may be used. Appropriate lysis conditions are described above Once a target protein and ligand interaction has been detected in a non-purified sample using the method of the invention, it may be desirable to identify the sequence or structure of the target protein, particularly if target protein variants have been investigated. Alternatively, as discussed above, the results obtained may be used to determine whether a drug therapy is likely to be effective in a patient and thus to tailor the therapy provided to a patient.

The binding of a high affinity drug to an established drug target, as shown in e.g. Examples 4, 5, 6 and 7, typically leads to a stabilisation of the target protein as supported by the positive shift of the melting temperature to a higher temperature. However, there are also ligands that, upon binding to the target protein, cause a negative shift of the melting temperature to a lower temperature, i.e. destabilisation. For example, negative shifts can be seen for ligands which form covalent-type bonds (including some metals) to a target protein. It is presumed that the binding energy of a covalent bond, and the energetically unfavourable strains generated by forming such a bond, could, in some cases, promote the destabilisation of a protein. For example, Ericsson et al (Anal Biochem 357 (2006) pp 289-298) show that compounds which contain heavy metal atoms, such as lutetium (III) chloride hexahydrate, are able to destabilise a number of bacterial proteins upon binding.

Thus, in a further aspect, the invention provides a method of determining whether a non-purified sample contains a target protein bound to a ligand of interest, wherein said ligand is not a fusion protein, comprising the steps of:
a) exposing said non-purified sample to a temperature which is capable of causing or enhancing precipitation of the target protein bound to said ligand to a greater extent than it is capable of causing or enhancing precipitation of the unbound target protein;
b) processing the product of step a) in order to separate soluble from insoluble protein; and
c) analysing either or both the soluble and insoluble protein fractions of step b) for the presence of target protein, wherein said target protein is not detected on the basis of enzymatic activity of a tag, peptide, polypeptide or protein fused thereto.

Another further aspect of the invention provides a method of determining whether a non-purified sample contains a target protein bound to a ligand of interest comprising the steps of:
a) exposing said non-purified sample to a temperature which is capable of causing or enhancing precipitation of the target protein bound to said ligand to a greater extent than it is capable of causing or enhancing precipitation of the unbound target protein;
b) processing the product of step a) in order to separate soluble from insoluble protein; and
c) analysing the soluble protein fraction of step b) for the presence of target protein, wherein said target protein is not detected on the basis of enzymatic activity of a tag, peptide, polypeptide or protein fused thereto.

In the above aspects, one would expose the non-purified sample to a temperature capable of causing or enhancing precipitation of the target protein bound to ligand, because the target protein bound to the destabilising ligand would precipitate at a lower temperature compared to the unbound target protein. Therefore, at the distinguishing temperature described in step a), one would expect to find more of the bound protein in the insoluble protein fraction, and more of the unbound protein in the soluble protein fraction.

Discussions of the various features of the methods of the invention and preferred embodiments set out in relation to stabilisation caused by ligand binding apply, mutatis mutandis, to these aspects of the invention where ligand binding causes destabilisation.

In some instances, there might be a physiological substrate or co-factor, such as ATP or NADP, present in a cell lysate, which binds to the target protein even before the ligand is added to the sample. When a ligand of interest is added to such a lysate, the shift of the melting curve towards higher temperatures will typically be smaller, as compared to the case when no physiological ligand is present in the lysate. In an extreme case, a very low affinity ligand (typically giving small positive thermal shifts) such as an early drug lead candidate, could at very high concentrations compete out a stronger physiological ligand (typically giving large positive thermal shifts) such as NADP. The replacement of the physiological ligand could, in such a case, lead to a negative shift, i.e. a shift to a lower melting temperature, when the apparent shift is the difference between the shifts of the two ligand bound forms of the protein. Under such circumstances, because the negative shift would be detectable as a decrease in the melting temperature of the target protein, the aspects of the invention relating to the ligand causing destabilisation would apply here.

The invention further encompasses an instrument for use in the methods of the invention wherein said instrument comprises a heating means, a means for separating soluble from insoluble protein and a means for analysing protein for the presence of target protein, e.g. for analysing suitable protein.

Alternatively viewed, an instrument adapted in use to carry out the method of the invention comprising a heating means, a means for separating soluble from insoluble protein and a means for analysing (e.g. soluble) protein for the presence of target protein, is encompassed.

Further, the invention is directed to the use of an instrument comprising a heating means, a means for separating soluble from insoluble protein and a means for analysing (e.g. soluble) protein for the presence of target protein in the methods of the invention.

The instruments are arranged such that a sample is first contacted with the heating means, then separation means and finally analysing means.

The term "a heating means" as used herein refers to any heat source which is capable of heating a sample to a particular temperature. Thus, the heating means may consist or comprise of a hot plate which can be programmed to heat a sample to a particular temperature, e.g. a PCR machine can be used to heat a sample in this way. Further, a heating means could comprise an incubator or a water bath.

The term "a means for separating soluble from insoluble protein" refers to any known apparatus which is capable of separating soluble and insoluble protein. Thus the means may comprise a filter paper where soluble protein will pass through the filter paper. Alternatively, the means may comprise an apparatus which is capable of imparting a centrifugal force on the heated sample e.g. a centrifuge. Additionally, the means may comprise an apparatus which is capable of affinity capture of the soluble protein. Such an apparatus may comprise antibodies or other affinity reagents which are capable of recognising the folded structure of the soluble protein. Antibodies, metal conjugates or other affinity reagents may be linked to magnetic beads or column resin. Insoluble protein can be removed by washing.

The term "means for analysing (e.g. soluble) protein for the presence of target protein" as used herein refers to any apparatus which would be capable of detecting the target protein. Thus this could refer to a mass spectrometer but more preferably may refer to the apparatus required to e.g. detect an antibody labelled with HRP or a fluorescent molecule bound to the target protein (i.e. nitrocellulose membrane or a fluorimeter). Further, the means for analysing protein for the presence of target protein may comprise an affinity column for binding target protein. The means for analysing protein for the presence of target protein may further comprise any of the reagents necessary to detect the target protein, or alternatively, these may be provided separately.

Finally, the present invention encompasses the use of a kit in the methods of the invention which comprises an antibody and/or a non-protein tag.

The invention will now be further described in the following non-limiting Examples in which:

FIG. 1 shows the assessment of the presence of soluble protein for three different proteins expressed in an *E. coli* sample after exposure to a range of different temperatures. The known melting temperatures of the purified proteins are shown on the right hand side of the figure.

FIG. 2 shows the assessment of the presence of soluble PIK3C3-protein after the addition of the ligands Wortmannin and 3-[4-(4-Morpholinyl)thieno[3,2-d]pyrimidin-2-yl]-phenol (Compound 15e) (+). Reference sample without added ligand are also shown (−). A thermal shift can be seen in the samples with ligands The lanes with proteins plus ligand are more thermally stable than proteins without ligand.

FIG. 3 shows the Western blot membranes of targets cyclin dependent kinase-2 (CDK-2) (a) and protein kinase C (PKC) (b). The dark bands indicate that the presence of soluble protein was detected up to a specific temperature and become fainter and ultimately disappear as the temperature is increased (from left to right). The pellet containing precipitated protein from the highest temperature was dissolved in loading buffer and loaded in the last lane of the gel in order to show the presence of the target protein in this fraction.

FIG. 4 shows the levels of soluble thymidylate synthase (TS), dihydrofolate reductase (DHFR), CDK-2 or PKC protein present after exposure to a range of different temperatures in mammalian cell extracts. The X axis represents the exposed temperature (° C.) and the Y axis represents the integrated intensity from the Western blots.

FIG. 5 shows the thermal melting curve from human cell extracts of soluble DHFR protein after the addition of the inhibitor methotrexate (♦). Reference sample without inhibitor is also shown (■). The X axis represents the exposed temperature (° C.) and the Y axis represents the integrated intensity from the Western blots.

FIG. 6 shows the thermal melting curve from human cell extracts of soluble TS protein after the addition of the inhibitor raltitrexed (+). Reference sample without inhibitor is also shown (•). The X axis represents the exposed temperature (° C.) and the Y axis represents the integrated intensity from the Western blots.

FIG. 7 shows the thermal melting curve of soluble methionine-aminopeptidase-2 after the addition of the ligand TNP-470 (x) either from cow liver extract (a) or from human cell extract (b). Reference sample without ligand is also shown (○). The X axis represents the exposed temperature (° C.) and the Y axis represents the integrated intensity from the Western blots.

Figure 10:
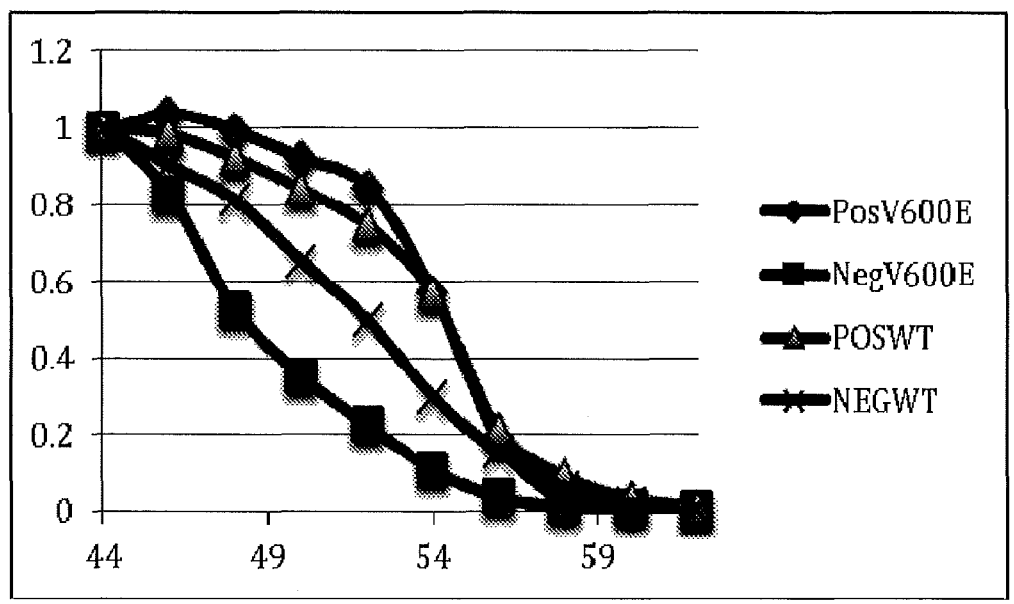

FIG. 10 shows the thermal melting curve of either soluble V600E variant B-raf protein (♦) or wild-type B-raf protein (▲) after the addition of the ligand SB590885. Reference samples without ligand are also shown, both for the V600E varient B-raf protein (■) and the wild-type B-raf protein (x). The X axis represents the exposed temperature (° C.) and the Y axis represents the integrated intensity from the Western blots.

Example 1

Determination of Melting Temperatures of Four Test Proteins

Three human soluble protein expression constructs in an expression vector with an N-terminal His-tag were used in order to determine the melting temperature of each protein in the cell. This was done by exposing the protein-containing cell to a panel of increasing temperatures and after each temperature step spotting the cells onto a "lysis/filtration sandwich" soaked in lysis buffer. By using this lysis/filtration step, the soluble protein (up to the protein's specific melting temperature) could be detected on a capturing nitrocellulose membrane as dark spots, whereas precipitated protein (i.e., above its specific melting temperature) was not able to pass through the filter membrane and could therefore not be detected.

Materials and Methods

Liquid cultures of *E. coli* cells overexpressing the three proteins of interest were started by inoculating 1 ml Luria-Bertani broth (LB) (Formedium Ltd., UK) containing 50 μg/ml kanamycin (Sigma-Aldrich Co., USA) and 35 μg/ml chloramphenicol (Duchefa Biochemie, The Netherlands) with frozen *E. coli* from glycerol stocks in a 96-well deep-well plate (Porvair Plc., UK). The cultures were incubated on a shaking board overnight at 700 rpm and +37° C. The following day 100 μl of each overnight culture was transferred to a corresponding well of a new 96-well deep-well plate containing 900 μl LB, 50 μg/ml kanamycin, and 35 μg/ml chloramphenicol. The cultures were incubated on a shaking board at 700 rpm and +37° C. After 1.5 hours the temperature was lowered to +18° C. (30 min.), and protein expression was induced by adding 100 mM IPTG (Anatrace/Affymetrix Co., USA). The cells were grown overnight on a shaking board at 700 rpm and +18° C. The cells were pelleted by centrifugation the following day at 1500 g for 2 min. and 900 μl supernatant was removed from each well by aspiration and discarded. The cell pellets were resuspended in the remaining 100 μl of medium (i.e., concentrated 10-fold). The cell suspensions were transferred to 8-tube PCR strips (Applied Biosystems, UK) and placed in a thermocycler. The following temperature program was used: +27° C.-+75° C. with 3° C. increments and a 3 min. hold at each step. After the 3 min. hold at each temperature the thermocycler was paused, and 2 μl of each cell suspension was quickly spotted onto a "lysis/filtration sandwich" consisting of Durapore filter membrane with 0.45 μm pore size (Millipore Inc., USA) (top layer), Protran BA 45 nitrocellulose membrane (Schleicher & Schuell, Germany) (middle layer), and 3MM Whatman paper (VWR Int'l. Ltd., UK). The "lysis/filtration sandwich" was soaked in native lysis buffer (20 mM Tris-HCl pH 8.0, 100 mM NaCl, 10 mg/ml Lysozyme (Sigma-Aldrich Co., USA), 25 U/μl Benzonase nuclease (Novagen, Denmark) and Complete protease inhibitor EDTA-free tablet (Roche, Switzerland). After spotting the cells onto the "lysis/filtration sandwich", the above-mentioned procedure was repeated at each temperature step. After spotting the last cell aliquot the "lysis/filtration sandwich" was incubated for 15 min. at room temperature in order to allow complete lysis and liquid cellular material transfer through the filter membrane. The "lysis/filtration sandwich" was thereafter frozen at −80° C. for 10 min. and then thawed for 10 min. at +37° C. This freeze/thaw procedure was repeated 3 times. The nitrocellulose membrane was blocked in TBST buffer (20 mM Tris-HCl pH 7.5, 500 mM NaCl, 0.05% Tween-20) containing 1% BSA (VWR Int'l. Ltd., UK) for 1 hour. The blot was then washed 3 times for 10 min. in TBST with some agitation (tabletop shaker). The membrane was incubated for 1 hour with INDIA HisProbe-HRP (Thermo Scientific, USA) diluted 1:5000 in TBST. The blot was then washed 3 times for 10 min. in TBST. Chemiluminescent detection of target protein expression level in each spot on the blot was performed using SuperSignal West Dura (Pierce) Extended Duration Substrate (Thermo Scientific, USA). Chemiluminescence was detected and recorded using a CCD camera (BioRad Laboratories, Inc., USA).

Results

Figure 1:
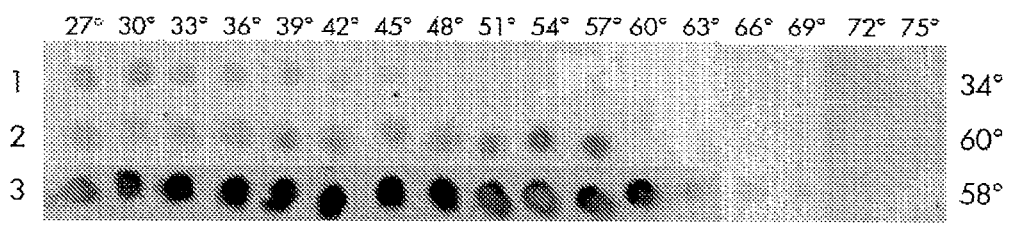

The dark spots indicating the presence of soluble protein were detected up to a specific temperature; they became fainter and ultimately disappeared at higher temperatures (FIG. 1). A comparison with previous data on the melting temperatures of the three IMAC-purified proteins (right panel) showed good correlation between the two sets of results. The melting points are not expected to be exact as the proteins have different solvent environment in a cell and in a purification buffer. This experiment shows that these proteins have distinct melting points in the cellular environment and that these melting points can be easily detected by monitoring the precipitation of the protein.

Example 2

Detection of an Increase of Melting Temperature after Binding to a Ligand

An expression construct of human soluble PIK3C3 protein in an expression vector with N-terminal His-tag was used to investigate a possible increase in melting temperature of the PIK3C3 construct after addition and binding of either of two PIK3C3 specific inhibitors; Wortmannin and Compound 15e. After treatment with or without one of the two inhibitors the cells expressing the PIK3C3 constructs were exposed to a panel of increasing temperatures and after each temperature step the cells expressing the proteins were spotted onto a "lysis/filtration sandwich" soaked in lysis buffer. By using this lysis/filtration step on the "lysis/filtration sandwich" the soluble protein (up to the construct's specific melting temperature) could be detected on a capturing nitrocellulose membrane as dark spots, whereas precipitated protein (i.e., above its specific melting temperature) was not able to pass through the filter membrane and could therefore not be detected. Melting temperatures of constructs treated with Compound 15e or Wortmannin were compared with those of untreated samples.

Materials and Methods

Liquid cultures of E. coli cells overexpressing PIK3C3 constructs were started by inoculating 1 ml Luria-Bertani broth (LB) (Formedium Ltd., UK) containing 50 μg/ml kanamycin (Sigma-Aldrich Co., USA) and 35 μg/ml chloramphenicol (Duchefa Biochemie, The Netherlands) with frozen E. coli from glycerol stocks in a 96-well deep-well plate (Porvair Plc., UK). The cultures were incubated on a shaking board overnight at 700 rpm and +37° C. The following day 100 μl of each overnight culture was transferred to a corresponding well of a new 96-well deep-well plate containing 900 μl LB, 50 μg/ml kanamycin, and 35 μg/ml chloramphenicol. The cultures were incubated on a shaking board at 700 rpm and +37° C. After 1.5 hours the temperature was lowered to +18° C. (30 min.), and protein expression was induced by adding 100 mM IPTG (Anatrace/Affymetrix Co., USA). The cells were grown overnight on a shaking board at 700 rpm and +18° C. The cells were pelleted by centrifugation the following day at 1500 g for 2 min. and 900 μl supernatant was removed from each well by aspiration and discarded. The cell pellets were resuspended in the remaining 100 μl of medium (i.e., concentrated 10-fold). For each of the experiments 1 mM of the PIK3C3 inhibitor Compound 15e (Santa Cruz Biotechnology, Inc., USA) or 500 μM Wortmannin (Santa Cruz Biotechnology, Inc., USA) dissolved in DMSO (Sigma-Aldrich Co., USA) or the equivalent volume (1 μl and 0.5 μl respectively) of pure DMSO was added and the samples were gently agitated for 30 min. at room temperature. The cell suspensions were transferred to 8-tube PCR strips (Applied Biosystems, UK) and placed in a thermocycler. The following temperature program was used: +27° C.-+75° C. with 3° C. increments and a 3 min. hold at each step. After the 3 min. hold at each temperature the thermocycler was paused, and 2 μl of each cell suspension was quickly spotted onto a "lysis/filtration sandwich" consisting of Durapore filter membrane with 0.45 μm pore size (Millipore Inc., USA) (top layer), Protran BA 45 nitrocellulose membrane (Schleicher & Schuell, Germany) (middle layer), and 3MM Whatman paper (VWR Int'l. Ltd., UK). The "lysis/filtration sandwich" was soaked in native lysis buffer (20 mM Tris-HCl pH 8.0, 100 mM NaCl, 10 mg/ml Lysozyme (Sigma-Aldrich Co., USA), 25 U/μl Benzonase nuclease (Novagen, Denmark) and Complete protease inhibitor EDTA-free tablet (Roche, Switzerland). After spotting the cells onto the "lysis/filtration sandwich", the abovementioned procedure was repeated at each temperature step. After spotting the last cell aliquot the "lysis/filtration sandwich" was incubated for 15 min. at room temperature in order to allow complete lysis and liquid cellular material transfer through the filter membrane. The "lysis/filtration sandwich" was thereafter frozen at −80° C. for 10 min. and then thawed for 10 min. at +37° C. This freeze/thaw procedure was repeated 3 times. The nitrocellulose membrane was blocked in TBST buffer (20 mM Tris-HCl pH 7.5, 500 mM NaCl, 0.05% Tween-20) containing 1% BSA (VWR Int'l. Ltd., UK) for 1 hour. The blot was then washed 3 times for 10 min. in TBST with some agitation (tabletop shaker). The membrane was incubated for 1 hour with INDIA His-Probe-HRP (Thermo Scientific, USA) diluted 1:5000 in TBST. The blot was then washed 3 times for 10 min. in TBST. Chemiluminescent detection of target protein expression level in each spot on the blot was performed using SuperSignal West Dura (Pierce) Extended Duration Substrate (Thermo Scientific, USA). Chemiluminescence was detected and recorded using a CCD camera (BioRad Laboratories, Inc., USA).

Results

Figure 2:
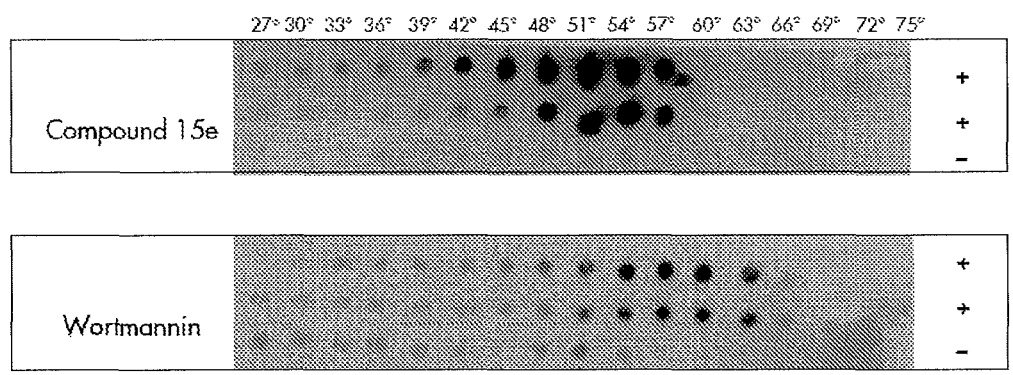

The dark spots indicating the presence of soluble protein were detected up to a specific temperature beyond which they where no longer visible (FIG. 2). Addition of Compound 15e resulted in an increased melting temperature from ca +55° to +58° C. whereas addition of Wortmannin resulted in an increased melting temperature between ca +55° and +65° C. A comparison with previous data on the melting temperatures of IMAC-purified PIK3C3 construct with and without the addition of Compound 15e or Wortmannin showed good correlation between the two sets of results. This experiment shows that it is possible to detect an increase in melting temperature of the PIK3C3 construct in the cellular environment after addition and binding of either of two PIK3C3 inhibitors Wortmannin and Compound 15e.

Example 3

Determination of Melting Temperature of Four Test Proteins in Mammalian Cell Systems In order to determine the melting temperature of four proteins, lysate was prepared from cultured mammalian cells and exposed to a panel of increasing temperatures. After the temperature steps, precipitated protein was removed, leaving only soluble protein (i.e. up to the protein's specific melting temperature) to be detected.

Materials and Methods

Lysate was prepared from cultured human adenocarcinoma cells (A549). Cells were disrupted on ice in hypotonic buffer and with homogenisation. The suspensions were freeze-thawed multiple times and all insoluble aggregates and cell debris were pelleted by centrifugation after completed lysis. The supernatant containing optically clear cytosolic fraction was aliquoted into 8-strip PCR tubes and subject to a panel of increasing temperatures. After heating for three minutes, the samples were cooled and precipitated protein was pelleted by centrifugation. The supernatant, containing soluble protein, was loaded on separating gels. In addition, the pellet containing precipitated protein from the highest temperature was dissolved in loading buffer and loaded in the last lane of the gel in order to show the presence of the protein in this fraction. The gels were blotted onto a Western blot nitrocellulose membrane. The membrane was washed and blocked with blocking reagent and probed with primary against dihydrofolate reductase (DHFR), thymidylate synthase (TS), cyclin dependent kinase-2 (CDK-2) and Protein Kinase C (PKC). Secondary antibodies were bound, and the signal from the bound secondary antibody was detected by chemiluminescence and recorded with a CCD camera. The intensities were measured and plotted.

Results

Figure 3A:
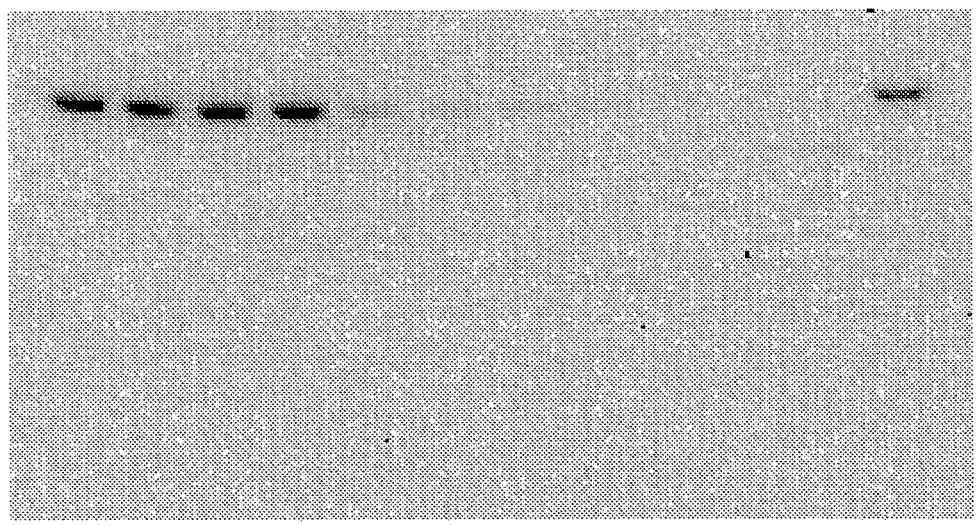
Figure 3B:
Figure 4:
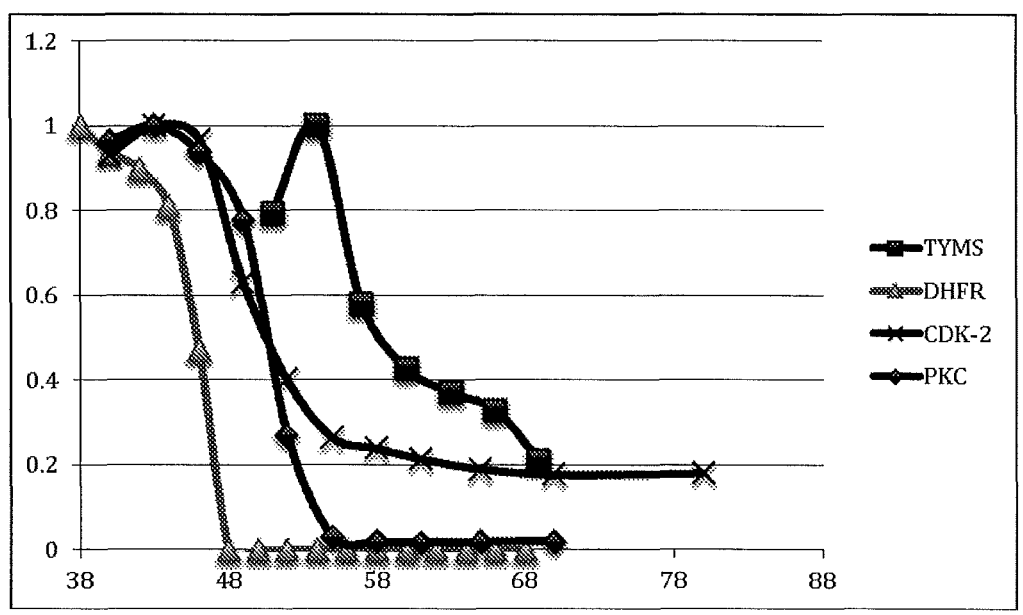

The dark bands indicating the presence of soluble protein were detected up to a specific temperature; they became fainter and ultimately disappeared at higher temperatures (FIG. 3). This experiment shows that these proteins have a distinct melting temperature and behaviour in the cellular environment and that these melting points can easily be detected by monitoring the precipitation of the protein (FIG. 4).

Example 4

Detection of an Increase of Melting Temperature after Binding to a Ligand in Mammalian Cells In order to investigate the possible increase or decrease in melting temperature after addition and binding of inhibitors, the proteins dihydrofolate reductase (DHFR) and thymidylate synthase (TS) were studied in cultured mammalian cells.

Lysate from cultured adenocarcinoma cells were treated with one of two inhibitors; raltitrexed or methotrexate, where the possible stabilising or destabilising effects of methotrexate was analysed for DHFR and raltitrexed was analysed for TS. After treatment with or without the inhibitors the samples were subjected to a heating step followed by removal of precipitated protein. The melting temperatures of treated samples were compared to those of untreated samples.

Materials and Methods

Lysate was prepared from cultured human adenocarcinoma cells (A549). Cells were disrupted on ice in hypotonic buffer and with homogenisation. The suspensions were freeze-thawed multiple times and all insoluble aggregates and cell debris were pelleted by centrifugation after completed lysis. The supernatant containing optically clear cytosolic fraction was divided into four aliquots, two were supplemented with their respective ligand with one corresponding negative control. The concentration of added ligand was 10 times the described IC50 value for the drug/target interaction. Each ligand was dissolved in DMSO and the final concentration was set to 1%.

After incubation, each aliquot was divided into 8-tube PCR strips and subjected to an array of temperatures ranging from +36° C. to 60° C. for DHFR and +51° C. to +69° C. for TS (guided by the melt curve from Example 3). After heating for three minutes, precipitated protein was pelleted by centrifugation. The resulting supernatants were loaded on a separating gel and transferred to a Western blot nitrocellulose membrane. After blocking of the membrane, it was probed with primary and secondary antibodies. The signal from the bound secondary antibody was detected by chemiluminescence and recorded with a CCD camera. The intensities were plotted to visualize the changes in melting temperature following ligand treatment.

Results

Figure 5:
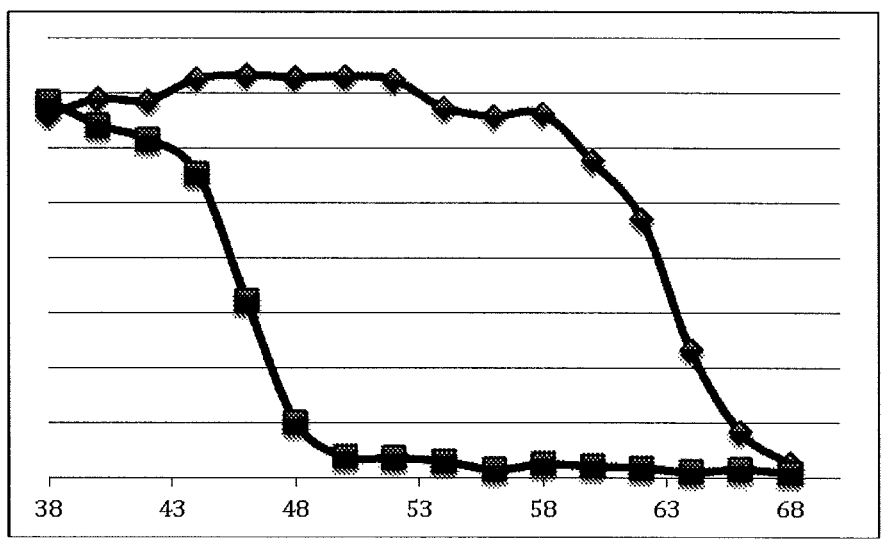
Figure 6:
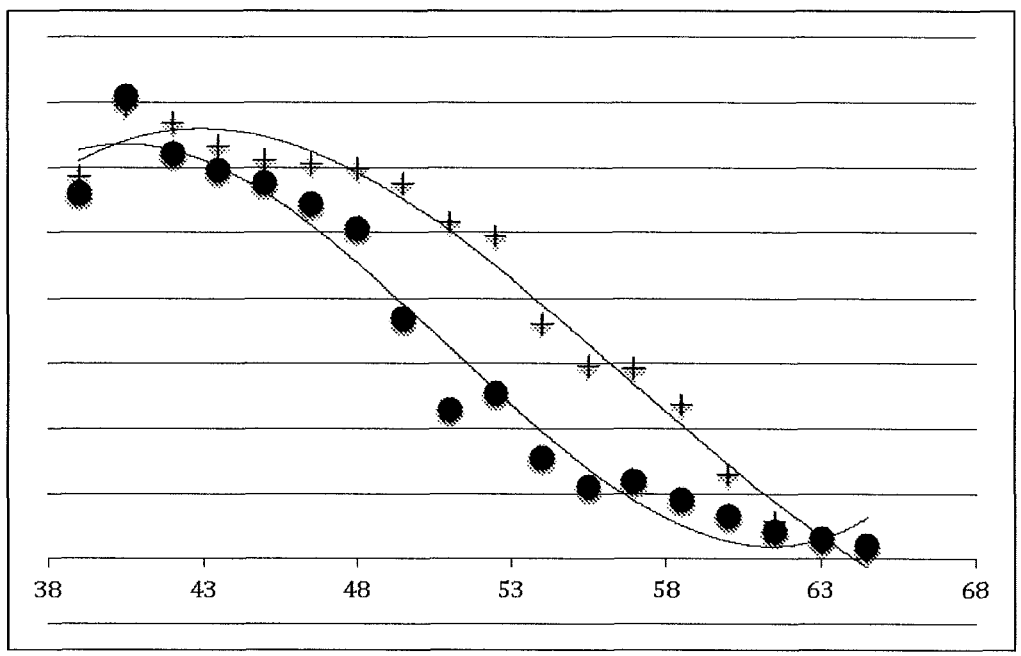

Addition of methotrexate or raltitrexed resulted in an increased melting temperature (FIGS. 5 and 6). This experiment shows that it is possible to detect an increase in melting temperature of DHFR or TS in the cellular environment after the addition and binding of the respective inhibitors methotrexate and raltitrexed.

Example 5

Cellular Thermal Shift Studied in Different Cell Systems and Organisms to Determine Changes in Melting Temperature Upon Binding of a Ligand In order to study the effects of ligand binding in different systems, the possible stabilising or destabilising effects upon addition of the ligand TNP-470, an antiangiogenic agent, to the protein methionine-aminopeptidase-2, was determined. Studies were done on cells from two different systems: a) intact cow liver biopsies incubated with TNP-470 and b) human cultured cells incubated with TNP-470. All samples were compared to reference samples, which had not been exposed to TNP-470. After treatment with or without the inhibitor, the samples were prepared and subjected to an array of increasing temperatures. The precipitated protein fraction was pelleted by means of centrifugation and the supernatant from each temperature step was analysed on gels and by Western blot. Melting temperatures of proteins treated with TNP-470 were compared to those of untreated samples.

Materials and Methods

Lysate was prepared for cultured human cells (K562) and cow liver samples by disruption on ice in hypotonic buffer and with homogenisation. The suspensions were freeze-thawed multiple times and all insoluble aggregates and cell debris were pelleted by centrifugation after completed lysis. The lysate of each cell type was divided into two aliquots, where one was supplemented with TNP-470 (dissolved in pure DMSO) and the other with an equivalent volume of pure DMSO. After incubation at room temperature the samples were divided into fractions of 50 microliters in 8-tube PCR strips and subsequently placed in a Veriti thermocycler.

Next, a series of temperatures were applied to different samples ranging between +56° C. to +88° C. with 2 or 4° C. increments and a 3 minute hold at each step. Following heating, the samples were cooled and the precipitated protein pelleted by centrifugation. 20 microliters of each supernatant was removed, supplemented with gel loading buffer and fully denatured by heating. The samples were loaded on a separating gel, which after full run time was blotted onto a nitrocellulose membrane. The membrane was washed and blocked with blocking reagent and probed with primary and secondary antibodies. The signal from the bound secondary antibody was detected by chemiluminescence and recorded with a CCD camera. The intensities were plotted to visualize the changes in melting temperature following ligand treatment.

Results

Figure 7A:
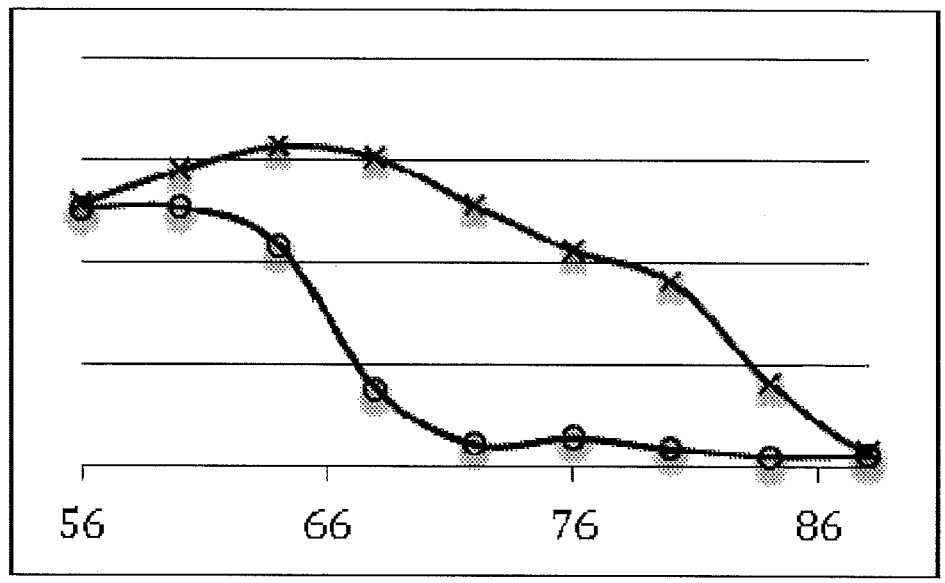
Figure 7B:
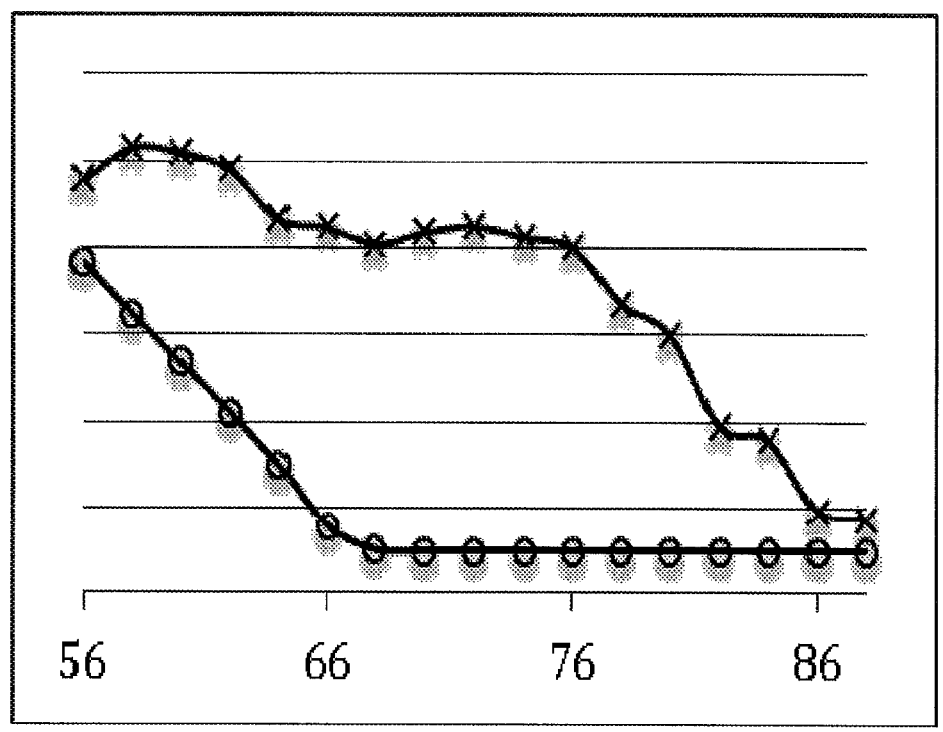

Dark bands on the Western blot membrane indicates the presence of soluble protein still in the supernatant. The soluble protein was detected up to a specific temperature beyond which they were no longer visible. Addition of TNP-470 resulted in a shift in melting temperature for human cell lysate from 62° C. to 80° C. (an 18° C. shift) and for cow liver lysate from 66° C. to 80° C. (a 14° shift) (FIG. 7).

Example 6

Dose Response Curve from the Concentration Dependence of the Thermal Stabilization For the purpose of constructing a dose-response curve to estimate apparent binding constants, cow liver lysate was subjected to a dilution series of ligand TNP-470, specifically targeting methionine aminopeptidase-2. Prior to this Example, curves corresponding to treated and untreated samples have been obtained (see Example 5) where the dose has been set at saturating levels. The differences in melting temperature can then be used to decide on a temperature where a treated sample is still present whilst an untreated sample will be precipitated. For this Example the temperature was set to +76° C. The dilution series was constructed as a series of 10-fold dilutions. The generated curve gives an indication of the concentration of the ligand needed to engage the target protein in the lysate.

Materials and Methods

Figure 8:
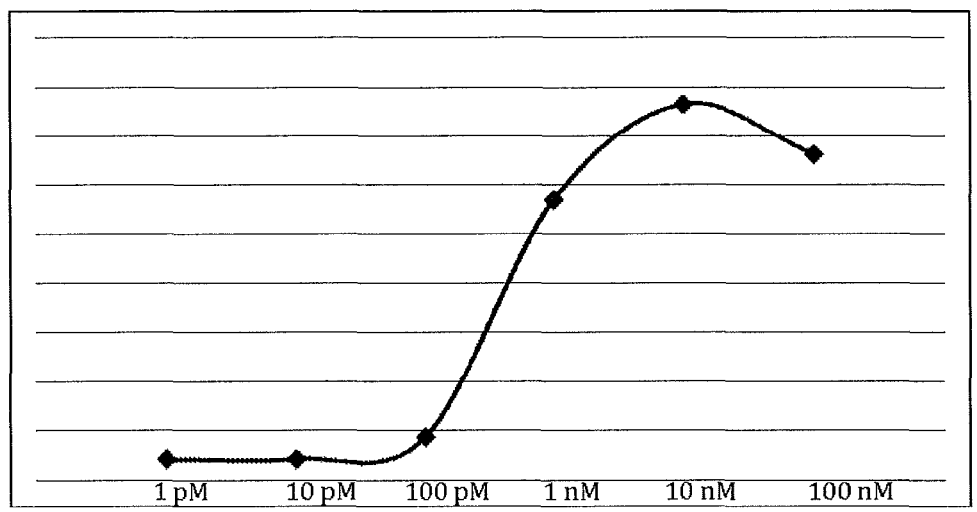
FIG. 8 shows the dose response curve of TNP-470 treatment of cow liver extract. The X axis represents the concentration of TNP-470 added and the Y axis represents the integrated intensity from the Western blots.

Lysate was prepared from cow liver samples. Cells were disrupted on ice in hypotonic buffer and with homogenisation. The suspensions were freeze-thawed multiple times and all insoluble aggregates and cell debris were pelleted by centrifugation after completed lysis. The supernatant containing optically clear cytosolic fraction was aliquoted into 8-strip PCR tubes where each tube contained an increasing amount of the ligand TNP-470 so that the concentration of ligand ranged between 1 picomolar and 100 nanomolar and with the DMSO concentration at 1% of the final volume. The samples were incubated and subsequently heated to 76° C. for 3 minutes. Following heat treatment the samples were cooled and the precipitated fraction was pelleted by centrifugation. 20 microliter of each supernatant was removed and supplemented with gel loading buffer and fully denatured by heating. The samples were loaded on a separating gel, which after full run time was blotted onto a nitrocellulose membrane. The membrane was washed and blocked with blocking reagent and probed with primary and secondary antibodies. The signal from the bound secondary antibody was detected by chemiluminescence and recorded with a CCD camera. The intensities were measured and plotted.
Results Dark bands on the Western blot membrane indicates presence of protein in the supernatant. If no or very little protein is present, no or very low signal will be visible. As the concentration of ligand increases, the amount of stabilised protein also increases. This is observed as a gradually increasing signal of the dark band on the Western blot membrane. Plotting the integrated intensities will render a dose-response curve (FIG. 8), which makes it possible to pinpoint an apparent concentration where half of the protein in the sample will have been engaged by a bound ligand (i.e. stabilised). This can have useful applications to set dosing regimes for patients or to find a therapeutic window for a drug by studies of apparent binding constants in different organs of the body.

Example 7

Biosensor Application—Measurement of Presence of a Ligand in Complex Fluids

The presence of a ligand (e.g. a drug) for which there is a cognate ligand binding protein (e.g. a drug target) can be indicated even in complex test samples lacking the target protein. This is achieved by adding an aliquot of a sample containing the protein (e.g. lysate of the target cell or a purified protein) to the biological fluid test sample. In line with Example 6, a dose response curve can also be constructed using serial dilutions of a biological fluid (e.g. blood plasma or serum) containing the ligand of interest. The curve thus created can be fitted on to a dose-response curve generated by spiking to give an estimated concentration of the ligand in the biological fluid.
Materials and Methods Lysate was prepared from cultured human adenocarcinoma cells (A549). Cells were disrupted on ice in hypotonic buffer and with homogenisation. The suspensions were freeze-thawed multiple times and all insoluble aggregates and cell debris were pelleted by centrifugation after completed lysis. The supernatant containing optically clear cytosolic fraction was aliquoted into 8-strip PCR tubes where each tube contained an increasing amount of the ligand TNP-470 dissolved in heat treated A549 lysate (heat treatment at 76° C. precipitated all target protein (methionine aminopeptidase-2) and ensured that no ligand would be consumed). As in Example 6, the concentrations ranged between 1 picomolar and 100 nanomolar effective concentration.

Figure 9:
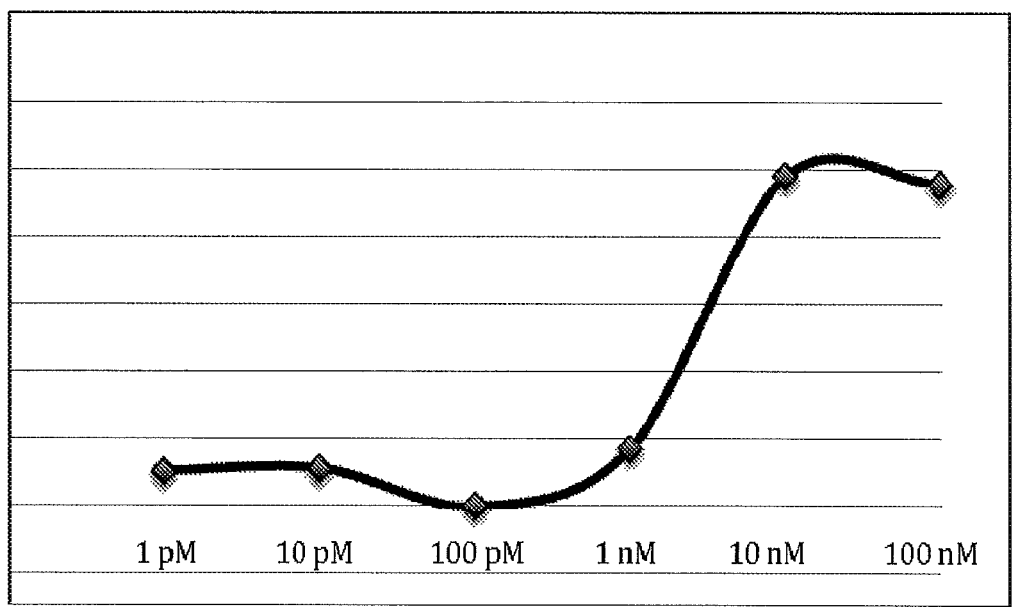
FIG. 9 shows the dose response curve of TNP-470 created by spiking with cell lysate containing target protein. The X axis represents the concentration of TNP-470 added and the Y axis represents the integrated intensity from the Western blots.

The samples where incubated and subsequently heated to 76° C. for 3 minutes. Following heat treatment the samples were cooled and the precipitated fraction was pelleted by centrifugation. 20 microliter of each supernatant was removed and supplemented with gel loading buffer and fully denatured by heating. The samples were loaded on a separating gel, which after full run time was blotted onto a nitrocellulose membrane. The membrane was washed and blocked with blocking reagent and probed with primary and secondary antibodies. The signal from the bound secondary antibody was detected by chemiluminescence and recorded with a CCD camera. The intensities were measured and plotted.
Results The heat-treated lysate was generated to mimic a biological fluid deficient in target protein. The spiking of the heat-treated lysate with ligand and the serial dilution thereof then produced a response curve (FIG. 9) that could be compared to and fitted on to an in vitro generated dose-response curve to get an estimate of how much ligand is present in the sample.

Example 8

Ligands Targeting Specific Protein Variants

Within a human population, proteins exist as different variants, usually with a small number of amino acid substitutions. In some instances these substitutions promote diseases, such as, for example, cancer. The protein B-raf is involved in pathways where disturbances in regulation or function can cause such diseases. Many different amino acid substitutions have been described for B-raf that result in an oncogenic protein. Amino acid substitutions can also make a protein less capable of binding drugs, which is one driving cause behind resistance development during cancer treatment.

The ligand SB590885 is known to bind the V600E variant of B-raf, which can be hard to treat with medication such as Sorafenib. In this Example, we show that there is a difference in stability in the substituted versus the wild type protein and that the binding of ligand affects the protein variants to a different extent.
Materials and Methods Lysate was prepared from cultured human A375 cells containing the V600E substitution in B-raf and K562, containing the wild type version thereof. Cells were disrupted on ice in hypotonic buffer and with homogenisation. The suspensions were freeze-thawed multiple times and all insoluble aggregates and cell debris were pelleted by centrifugation after completed lysis. The supernatants containing optically clear cytosolic fraction were each aliquoted into two tubes where each tube contained either the ligand SB590885 dissolved in DMSO or pure DMSO for control. The samples where incubated and subsequently aliquoted into 8-tube PCR strips in fractions of 50 microliters. A series of temperatures were applied to the different samples ranging between +44° C. to +62° C. with 2° C. increments and a 3 minute hold at each temperature. Following heating, the samples were cooled and the precipitated protein pelleted by centrifugation. 20 microliter of each supernatant was removed and supplemented with gel loading buffer and fully denatured by heating. The samples were loaded on a separating gel, which after full run time was blotted onto a nitrocellulose membrane. The membrane was washed and blocked with blocking reagent and probed with primary and secondary antibodies. The signal from the bound secondary antibody was detected by chemiluminescence and recorded with a CCD camera. The intensities were normalized and plotted to visualize the changes in melting temperature following ligand treatment (FIG. 10).
Results The melting curves in FIG. 10 show that substituted V600E B-raf is less stable than wild type if no stabilising ligand is present. Upon treatment, V600E substituted B-raf is stabilised with approximately a 6° C. increase in the melting temperature, while the wild type protein once stabilised only showed a 3° C. increase in the melting temperature. After stabilisation, both the V600E B-raf and the wild-type B-raf showed a melting temperature of 55° C.

The invention claimed is:

1. A method of determining whether a non-purified sample contains a target protein bound to a ligand of interest comprising the steps of:
   a) exposing the non-purified sample to a temperature which is capable of causing or enhancing precipitation of the unbound target protein to a greater extent than it is capable of causing or enhancing precipitation of the target protein bound to the ligand wherein the target protein in said non-purified sample is comprised within or on a cell;
   b) subjecting said sample to conditions capable of causing cell lysis;
   c) separating soluble from insoluble protein in the product of step b); and
   d) analyzing either or both the soluble and insoluble protein fractions of step c) for the presence of the target protein, wherein the target protein is detected by affinity binding a detection moiety or by mass spectrometry.

2. The method of claim 1, wherein according to step d) the soluble fraction is analysed.

3. The method of claim 1, wherein the non-purified sample is a cell colony, a liquid culture of cells, or a patient or animal sample.

4. The method of claim 1, wherein the ligand is a protein, DNA molecule, RNA molecule, a cellular metabolite, a drug, or another chemical.

5. The method of claim 1, wherein the temperature is equal to or greater than the initial melting temperature of the target protein.

6. The method of claim 1, wherein the temperature is greater than 40° C.

7. The method of claim 1 wherein, the non-purified sample is exposed to a series of different temperatures, including a temperature which is equal to or greater than the initial melting temperature of the target protein.

8. The method of claim 1, wherein the target protein is identified using antibodies.

9. The method of claim 1, wherein the separating step c) is a step of centrifugation, filtration or affinity separation.

10. The method of claim 9, wherein the target protein in the filtrate from the filtration step is captured on a solid support prior to the analysis step d).

11. The method of claim 1, wherein the target protein is added to the sample in order to determine the presence or absence of the ligand of interest in the sample.

12. The method of claim 1, wherein a ligand of interest is added to the sample in order to determine the presence or absence of the target protein in the sample.

13. A method of determining whether a non-purified sample contains a target protein bound to a ligand of interest, wherein the ligand is not a fusion protein, comprising the steps of:
   a) exposing the non-purified sample to a temperature which is capable of causing or enhancing precipitation of the target protein bound to the ligand to a greater extent than it is capable of causing or enhancing precipitation of the unbound target protein wherein the target protein in said non-purified sample is comprised within or on a cell;
   b) subjecting said sample to conditions capable of causing cell lysis;
   c) separating soluble from insoluble protein in the product of step b); and
   d) analysing either or both the soluble and insoluble protein fractions of step c) for the presence of the target protein, wherein the target protein is detected by affinity binding a detection moiety or by mass spectrometry.

14. The method of claim 13, wherein the target protein is identified using antibodies, and wherein step c) is a step of centrifugation, filtration or affinity separation.

15. The method of claim 13, wherein the target protein is not detected on the basis of enzymatic activity of a tag, peptide, polypeptide or protein fused thereto.

16. The method of claim 3, wherein the patient or animal sample is obtained directly from the patient or animal and/or is a tissue sample.

17. The method of claim 16 wherein the tissue sample is blood, serum, plasma or lymph.

18. The method of claim 1, wherein the non-purified sample is a cell colony, separation step c) is filtration, and wherein said cell colony is lifted on a filler and lysis is carried out directly on the colony on the filler.

* * * * *

UNITED STATES PATENT AND TRADEMARK OFFICE
CERTIFICATE OF CORRECTION

PATENT NO.       : 8,969,014 B2  
APPLICATION NO.  : 14/057920  
DATED            : March 3, 2015  
INVENTOR(S)      : Pär Nordlund Page 1 of 1

It is certified that error appears in the above-identified patent and that said Letters Patent is hereby corrected as shown below:

In the Claims:

At column 30, claim number 18, line numbers 37-40, please replace claim 18, which reads:

"The method of claim 1, wherein the non-purified sample is a cell colony, separation step c) is filtration, and wherein said cell colony is lifted on a filler and lysis is carried out directly on the colony on the filler."

with the following:

--The method of claim 1, wherein the non-purified sample is a cell colony, separation step c) is filtration, and wherein said cell colony is lifted on a filter and lysis is carried out directly on the colony on the filter.--

Signed and Sealed this  
Sixteenth Day of June, 2015

Michelle K. Lee  
*Director of the United States Patent and Trademark Office*